US011499178B2

(12) United States Patent
Sasaki et al.

(10) Patent No.: US 11,499,178 B2
(45) Date of Patent: Nov. 15, 2022

(54) LABELING METHOD FOR NUCLEIC ACID

(71) Applicants: Kyushu University, National University Corporation, Fukuoka (JP); Kurume Research Park Co., Ltd., Fukuoka (JP)

(72) Inventors: Shigeki Sasaki, Fukuoka (JP); Yosuke Taniguchi, Fukuoka (JP); Gakuro Harada, Fukuoka (JP)

(73) Assignees: Kyushu University, National University Corporation, Fukuoka (JP); Kurume Research Park Co., Ltd., Kurume (JP)

( * ) Notice: Subject to any disclaimer, the term of this patent is extended or adjusted under 35 U.S.C. 154(b) by 207 days.

(21) Appl. No.: 16/798,704

(22) Filed: Feb. 24, 2020

(65) Prior Publication Data
US 2020/0308635 A1 Oct. 1, 2020

(30) Foreign Application Priority Data

Mar. 29, 2019 (JP) .............................. JP2019-065888

(51) Int. Cl.
| C12P 19/34 | (2006.01) |
| C12Q 1/6816 | (2018.01) |
| C07H 21/00 | (2006.01) |
| C12Q 1/6827 | (2018.01) |
| C12Q 1/6837 | (2018.01) |
| C07H 21/02 | (2006.01) |

(52) U.S. Cl.
CPC ........... *C12Q 1/6816* (2013.01); *C07H 21/00* (2013.01); *C12Q 1/6827* (2013.01); *C12Q 1/6837* (2013.01); *C12Q 2600/158* (2013.01)

(58) Field of Classification Search
None
See application file for complete search history.

(56) References Cited

PUBLICATIONS

Shigeki Sasaki, "8. Innovative technology for targeting RNA based on the intelligent nonnatural oligonucleotides" The Uehara Memorial Foundation Research Report, vol. 30, 2016, pp. 1-8. (Year: 2016).*
Office Action dated Jul. 14, 2021 issued in corresponding Korean patent application No. 10-2020-0023221.
Shigeki Sasaki, "Development of Novel Functional Molecules Targeting DNA and RNA", Chemical and Pharmaceutical Bulletin, 2019, vol. 67 (6), pp. 505-518.
Dolle, F., et al., "A general method for labeling oligodeoxynucleotides with 18F for in vivo PET imaging", J. Label. Compd. Radiopharm., 1997, 39, 319-330.
Hatanaka, K., et al., "Development of double-stranded siRNA labeling method using positron emitter and its in vivo trafficking analyzed by positron emission tomography", 2010, Bioconjugate Chem., 2010, vol. 21, pp. 756-763.
Kuboyama, T., et al., "Stoichiometry-focused 18F-labeling of alkyne-substituted oligodeoxynucleotides using azido ([18F]fluoromethyl)benzenes by Cu-catalyzed Huisgen reaction", Bioorg. Med. Chem., 2011, 19, pp. 249-255.
Bartlett, D. W. et al., "Impact of tumor-specific targeting on the biodistribution and efficacy of siRNA nanoparticles measured by multimodality in vivo imaging", Proc Natl Acad Sci USA, 2007, vol. 104, pp. 15549-15554.
Liu, G., et al., "Tumor pretargeting in mice using 99mTc-labeled morpholino, a DNA analog", J. Nucl. Med., 2002, vol. 43, pp. 384-391.
Roivainen, A., et al., "68Ga-labeled oligonucleotides for in vivo imaging with PET", J. Nucl. Med., 2004, vol. 45, pp. 347-355.
Tan, W., et al., "Site-specific synthesis of [3H]oligonucleotides in high specific activity through direct solid-phase redox chemistry", Tetrahedron Lett., 1995, vol. 36, No. 21, pp. 3631-3634.
Christensen, J., et al., "Tritium labeling of full-length small interfering RNAs", J. Label. Compd. Radiopharm., 2012, 55, pp. 189-196.
Dougan, H., et al., "Synthesis and radioiodination of a stannyl oligodeoxyribonucleotide", Nucleic Acids Res., 1997, vol. 25, pp. 2897-2901.
Fujibayashi, Y., et al., "A novel 111In-labeled antisense DNA probe with multi-chelating sites (MCS-Probe) showing high specific radioactivity and labeling efficiency", Nucl. Med Biol, 1999, vol. 26, pp. 17-21.
Office Action dated Mar. 9, 2021, issued for the corresponding JP patent application No. 2019-065888.
Shigeki Sasaki et al., "The oligodeoxynucleotide probes for the site-specific modification of RNA", Chemical Society Reviews, 2011, vol. 40 (12), pp. 5698-5706.
Shigeki Sasaki, "8. Innovative technology for targeting RNA based on the intelligent nonnatural oligonucleotides", The Uehara Memorial Foundation Research Report, 2016, vol. 30, pp. 1-6.
Masaru Hasegawa, "The Syntheses of Labelled Compounds", Synthetic Organic Chemistry, 1967, vol. 25 (2), pp. 116-126 (see Office Action cited above regarding brief explanation of the relevancy of the teachings of this art).
Extended European Search Report (EESR) dated Jul. 9, 2020, issued for the corresponding EP patent application No. 20159534 5.
Daichi Jitsuzaki et al., "Remarkable acceleration of a DNA/RNA inter-strand functionality transfer reaction to modify a cytosine residue: the proximity effect via complexation with a metal cation", Nucleic Acids Research, vol. 42, No. 13, Jun. 23, 2014, pp. 8808-8815, XP055703786, ISSN: 0305-1048, DOI: 10.1093/nar/gku538, Figure 1.

(Continued)

*Primary Examiner* — Bradley L. Sisson
(74) *Attorney, Agent, or Firm* — Maschoff Brennan; Yuefen Zhou; Brent A. Johnson

(57) ABSTRACT

Provided is a labeling method for nucleic acid including a reaction step for hybridizing a nucleic acid probe that has a nucleotide sequence complementary to that of a nucleic acid to be labeled and contains a reactive nucleobase derivative incorporated at a position complementary to that of a target nucleobase as a target of labeling in the nucleic acid to be labeled, to the nucleic acid to be labeled; a transferring step for transferring a transfer group contained in the reactive nucleobase derivative to the nucleotide residue containing the target nucleobase in the nucleic acid to be labeled; and a labeling step for labeling the transfer group transferred to the nucleotide residue with a radioactive material.

5 Claims, 5 Drawing Sheets

Specification includes a Sequence Listing.

(56) References Cited

PUBLICATIONS

Bertrand Kühnast et al., "General Method to Label Antisense Oligonucleotides with Radioactive Halogens for Pharmacological and Imaging Studies", Bioconjugate Chemistry, vol. 11, No. 5, Sep. 1, 2020, pp. 627-636, XP055703812, US ISSN: 1043-1802, DOI: 10.1021/bc990183i.

Qibing Zhou et al., "A general strategy for target-promoted alkylation in biological systems", Proceedings of the National Academy of Sciences, vol. 100, No. 26, Jan. 1, 2003, pp. 15452-15457, XP055049075, ISSN: 0027-8424, DOI: 10.1073/pnas.2533112100, Figure 2.

Clifford S. Rossiter et al., "Few constraints limit the design of quinone methide-oligonucleotide self-adducts for directing DNA alkylation", Chemical Communications, vol. 47, No. 5, Jan. 1, 2011, pp. 1476-1478, XP055703249, ISSN: 1359-7345, DOI: 10.1039/c0cc03317k, Scheme 1.

Norihiro Sato et al., "A new strategy for site-specific alkylation of DNA using oligonucleotides containing an abasic site and alkylating probes", Chemical Communications, vol. 51, No. 80, Jan. 1, 2015, pp. 14885-14888, XP055703759, ISSN: 1359-7345, DOI: 10.1039/c5cc03915k, Figure 1.

Jonathan Lotze et al., "Peptide-tags for site-specific protein labelling in vitro and in in vivo", Molecular Biosystems, vol. 12, No. 6, Jan. 1, 2016, pp. 1731-1745, XP055340848, GB ISSN: 1742-206X, DOI: 10.1039/c6mb00023a.

\* cited by examiner

UNMODIFIED RNA

NONRADIOACTIVELY LABELED RNA 03

LABELING METHOD FOR NUCLEIC ACID

CROSS-REFERENCE TO RELATED APPLICATION

This application claims the benefit of Japanese Patent Application No. 2019-65888, filed on Mar. 29, 2019, the entire disclosure of which is incorporated by reference herein.

SEQUENCE LISTING

The instant application contains a Sequence Listing which has been submitted electronically in ASCII format and is hereby incorporated by reference in its entirety. Said ASCII copy, created on Feb. 24, 2020, is named 19F082-US_Sequence_Listing.txt, and is 2,095 bytes in size.

FIELD

This application relates generally to a labeling method for nucleic acid.

BACKGROUND

Nucleic acid drugs, such as antisense, aptamer, and siRNA drugs, exert effects by specific base-pairing between the short DNA or RNA fragments in the nucleic acid drugs and RNA from disease related genes. Such nucleic acid drugs can target not only protein-coding regions but also non-protein-coding regions in RNA transcripts. Nucleic acid drugs are being developed as medicines for diseases that are not successfully treated with small-molecule and antibody drugs, and are being studied in many clinical trials for refractory diseases such as genetic disorders and cancers.

Each antisense drug in practical use comprises many chemically modified nucleotides to prevent in vivo enzymatic hydrolysis. However, side effects or toxicity from the chemically modified nucleotides have become a big problem. In contrast to antisense drugs comprising many chemically modified nucleotides, siRNAs are mostly derived from naturally occurring nucleic acids in connection with the mechanism of action. Thus, siRNA drugs are incorporated into any of drug delivery systems (DDSs) to prevent in vivo degradation and the resulting drugs are used. However, since some DDSs can cause toxicity, avoiding toxicities not only from siRNAs but also from DDSs is needed.

The pharmacokinetics of small-molecule drugs are studied during the development stage to improve efficacy and to avoid toxicity. The pharmacokinetic analyses of nucleic acid drugs have not been performed well as compared to those conducted for the development of small-molecule drugs. This is because those nucleic acid drugs typically have such a high molecular weight of several thousand daltons (Da) and will produce metabolites with such a wide variety of structures that the nucleic acid drugs are not applicable to, for example, mass spectrometric and HPLC analyses. Especially in cases of siRNA drugs, an activated RNA-induced silencing complex (RISC) which has incorporated an antisense strand of a siRNA exhibits its effect at quite low concentrations in cells. Thus, the nucleic acids subject to a pharmacokinetic analysis are often reduced to very low concentrations at or below the limit of detection.

Since radioactivity can be sensitively detected, radioactivity can be used not only in in vivo experiments but also used for tracking a labeled nucleic acid in human subjects by PET (positron emission tomography) and SPECT (single photon emission computed tomography) imaging.

Radioactively labeled nucleic acids, namely radiolabeled nucleic acids, include end-labeled nucleic acids, in which either end of each nucleotide sequence is labeled, and internally labeled nucleic acids, in which a non-terminal portion of each nucleotide sequence is labeled. End-labeled nucleic acids are disclosed in Non Patent Literature 1 (Dolle, F., and four other authors, "A general method for labeling oligodeoxynucleotides with $^{18}$F for in vivo PET imaging", J. Label. Compd. Radiopharm., 1997, 39, 319-330); Non Patent Literature 2 (Hatanaka, K., and seven other authors, "Development of double-stranded siRNA labeling method using positron emitter and its in vivo trafficking analyzed by positron emission tomography", Bioconjugate Chem., 2010, 21, 756-763); Non Patent Literature 3 (Kuboyama, T., and 10 other authors, "Stoichiometry-focused $^{18}$F-labeling of alkyne-substituted oligodeoxynucleotides using azido([$^{18}$F]fluoromethyl)benzenes by Cu-catalyzed Huisgen reaction", Bioorg. Med. Chem., 2011, 19, 249-255); Non Patent Literature 4 (Bartlett, D. W., and four other authors, "Impact of tumor-specific targeting on the biodistribution and efficacy of siRNA nanoparticles measured by multimodality in vivo imaging", Proc Natl Acad Sci USA, 2007, 104, 15549-15554); Non Patent Literature 5 (Liu, G., and five other authors, "Tumor pretargeting in mice using $^{99m}$Tc-labeled morpholino, a DNA analog", J. Nucl. Med., 2002, 43, 384-391); and Non Patent Literature 6 (Roivainen, A., and 11 other authors, "$^{68}$Ga-labeled oligonucleotides for in vivo imaging with PET", J. Nucl. Med., 2004, 45, 347-355). In cases of end-labeled nucleic acids, these nucleic acids are degraded in vivo to fragments, among which only fragments containing a radiolabel at either end can be detected. Thus, end-labeled nucleic acids are suitable for pharmacokinetic analysis of antisense drugs which are protected from degradation as described above.

In contrast, siRNAs which are mostly derived from naturally occurring nucleic acids are prone to fragmentation by enzymatic hydrolysis, and the sense strands remaining unincorporated into RISCs during the process of forming activated RISCs will be degraded and metabolized. Thus, internally labeled nucleic acids in which a nucleotide at a position of interest is selectively radiolabeled are essential to detect the incorporation of siRNA into activated RISC and to analyze the dynamics of the incorporation.

Internally labeled nucleic acids can be prepared using a photoreactive agent, such as psoralen, or a polymerase. However, use of a photoreactive agent or a polymerase allows a nucleic acid to be labeled at random but not to be selectively radiolabeled at positions of interest within the nucleic acid sequence.

Internally labeled nucleic acids are reported in Non Patent Literature 7 (Tan, W., and three other authors, "Site-specific synthesis of [$^3$H]oligonucleotides in high specific activity through direct solid-phase redox chemistry", Tetrahedron Lett., 1995, 36, 21, p. 3631-3634); Non Patent Literature 8 (Christensen, J., and five other authors, "Tritium labeling of full-length small interfering RNAs", J. Label. Compd. Radiopharm., 2012, 55, 189-196); Non Patent Literature 9 (Dougan, H., and three other authors, "Synthesis and radioiodination of a stannyl oligodeoxyribonucleotide", Nucleic Acids Res., 1997, 25, p. 2897-2901); and Non Patent Literature 10 (Fujibayashi, Y., and seven other authors, "A novel $^{111}$In-labeled anti sense DNA probe with multi-chelating sites (MCS-Probe) showing high specific radioactivity and labeling efficiency", Nucl. Med. Biol., 1999, 26, p. 17-21). In any of these internally labeled nucleic acids, a labeling precursor is incorporated into the nucleic acid during synthesis, and a radioisotope is then introduced into the precursor after completion of the nucleic acid synthesis. Non Patent Literature 7 discloses a method in which the 5' hydroxyl group of the ribose of a nucleotide of interest is oxidized and the oxidized ribose is then reduced with tritium-labeled sodium borohydride during solid-phase nucleic acid synthesis using a nucleic acid synthesizer.

Non Patent Literature 8 discloses a method in which the Br of a bromouracil incorporated during siRNA synthesis is allowed to react with tritium gas under pressure for bromine/tritium exchange. The radioisotope used for the preparation of internally labeled nucleic acids is not limited to tritium. For example, an isotope of iodine is used in Non Patent Literature 9. Moreover, Non Patent Literature 10 discloses a method in which a metal complex containing an isotope of indium is incorporated into a nucleic acid.

As seen in the cases of the internally labeled nucleic acids reported in Non Patent Literature 7 to Non Patent Literature 10, where a labeling precursor should be incorporated during synthesis of the nucleic acids, the disclosed methods are not applicable to labeling of nucleic acids which are previously synthesized or isolated from natural systems. Additionally, the method disclosed in Non Patent Literature 9 requires reaction with tritium gas under pressure, which results in limited number of institutions that can practice the method. Furthermore, the internally labeled nucleic acid prepared using a metal complex and disclosed in Non Patent Literature 10 is so sterically bulky that the function of the nucleic acid may be compromised.

The present disclosure is completed in view of the above-described problems. The aim of the present disclosure is to provide a labeling method for nucleic acid by which a nucleic acid, whether of synthetic or natural origin, can be labeled without compromising the function thereof in such a manner that the labeled nucleic acid can be sensitively detected even when the labeled nucleic acid is fragmented.

SUMMARY

A labeling method for nucleic acid according to the present disclosure includes:

a reaction step for hybridizing a nucleic acid probe that has a nucleotide sequence complementary to that of a nucleic acid to be labeled and contains a reactive nucleobase derivative incorporated at a position complementary to that of a target nucleobase as a target of labeling in the nucleic acid to be labeled, to the nucleic acid to be labeled;

a transferring step for transferring a transfer group contained in the reactive nucleobase derivative to the nucleotide residue containing the target nucleobase in the nucleic acid to be labeled; and a labeling step for labeling the transfer group transferred to the nucleotide residue with a radioactive material.

In that case, the transfer group may be a pyridinyl-keto transfer group, and the pyridinyl-keto transfer group may be transferred to a cytosine or adenine nucleobase as the target nucleobase during the transferring step.

In addition, the transfer group may be a diketo transfer group, and the diketo transfer group may be transferred to a guanine nucleobase as the target nucleobase during the transferring step.

In addition, the transfer group may be acetyl group, and an acetyl group may be transferred to the 2' position of the ribose of a nucleotide residue containing an uracil nucleobase as the target nucleobase during the transferring step.

In addition, the labeling method for nucleic acid according to the present disclosure may further include:

a first step for hybridizing a nucleic acid probe that has a nucleotide sequence complementary to that of the nucleic acid to be labeled and contains a reactive nucleobase derivative incorporated at a position complementary to that of a nucleobase different from the position of the target nucleobase in the nucleic acid to be labeled, to the nucleic acid to be labeled;

a second step for transferring a transfer group contained in the reactive nucleobase derivative of the nucleic acid probe, which is hybridized in the first step to the nucleic acid to be labeled, to the nucleotide residue containing the nucleobase located at the different position in the nucleic acid to be labeled; and a third step for labeling the transfer group transferred to the nucleotide residue, which contains the nucleobase located at the different position, with a kind of radioactive material different from the radioactive material used in the labeling step.

In addition, the radioactive material may be tritium.

A nucleic acid, whether of synthetic or natural origin, can be labeled by the present disclosure without compromising the function thereof in such a manner that the labeled nucleic acid can be sensitively detected even when the labeled nucleic acid is fragmented.

BRIEF DESCRIPTION OF THE DRAWINGS

A more complete understanding of this application can be obtained when the following detailed description is considered in conjunction with the following drawings, in which.

DETAILED DESCRIPTION

Figure 1A:
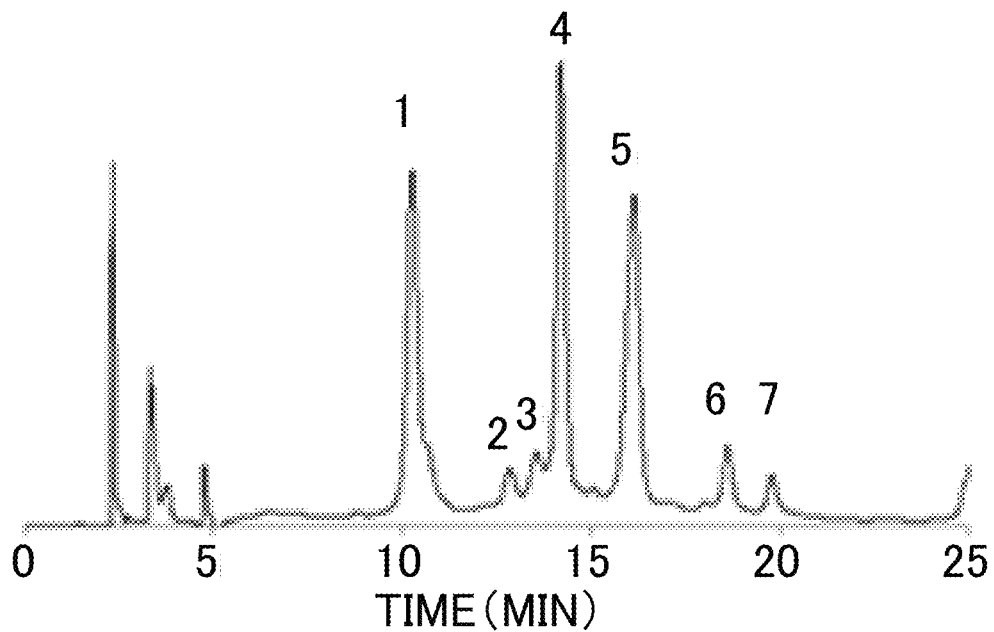
FIG. 1A shows the result of purification of the labeled sense strand of a siRNA according to Example 1 by high performance liquid chromatography (HPLC), in which ultraviolet (UV) peaks corresponding to crude reaction products are illustrated.

An embodiment of the present disclosure will be described with reference to the drawings. However, the present disclosure will not be limited by the following embodiment.

Embodiments

A labeling method for nucleic acid according to the present embodiment includes a reaction step, a transferring step, and a labeling step. In the reaction step, a nucleic acid probe is hybridized to a nucleic acid to be labeled. The nucleic acid to be labeled is not particularly limited, provided that 2'-deoxyribonucleotides can form a duplex with the nucleic acid. For example, DNA, RNA, and modified products thereof are included in the nucleic acid to be labeled. Preferably, the nucleic acid to be labeled is RNA. More specifically, the nucleic acid to be labeled is, for example, single-stranded DNA, double-stranded DNA, single-stranded RNA, double-stranded RNA, antisense strand, siRNA, or mRNA. The nucleotide sequence of the nucleic acid to be labeled is not particularly limited, and a nucleic acid with any nucleotide sequence can be a nucleic acid to be labeled. Preferably, the nucleotide sequence of the nucleic acid to be labeled includes at least one guanine nucleobase, cytosine nucleobase, or adenine nucleobase.

The sequence of the nucleic acid to be labeled is not limited to a particular length, and is, for example, 5 to 1000 nucleotides long, 8 to 500 nucleotides long, 10 to 300 nucleotides long, or 10 to 200 nucleotides long. The sequence of the nucleic acid to be labeled is preferably 10 to 150 nucleotides long, 15 to 100 nucleotides long, or 20 to 100 nucleotides long.

The nucleic acid probe is an oligonucleotide with a nucleotide sequence which is complementary to that of the nucleic acid to be labeled. In the nucleic acid probe, a reactive nucleobase derivative is incorporated at a position complementary to that of a target nucleobase as a target of labeling in the nucleic acid to be labeled.

In cases where the target nucleobase is guanine, the reactive nucleobase derivative incorporated into the nucleic acid probe is, for example, S-(2-(methylidene)-1-phenylbutane-1,3-dione)-6-thioguanine (derivative 1) represented by the structural formula (1).

[Chem 1]

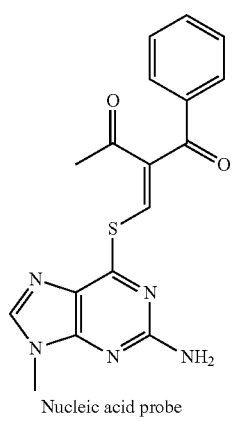

(1)

Nucleic acid probe

In cases where a cytosine in the nucleic acid to be labeled is selectively labeled, the reactive nucleobase derivative incorporated into the nucleic acid probe is, for example, (E)-3-(1-(pyridin-2-yl)prop-2-en-1-one)-6-thioguanine (derivative 2) represented by the structural formula (2).

[Chem 2]

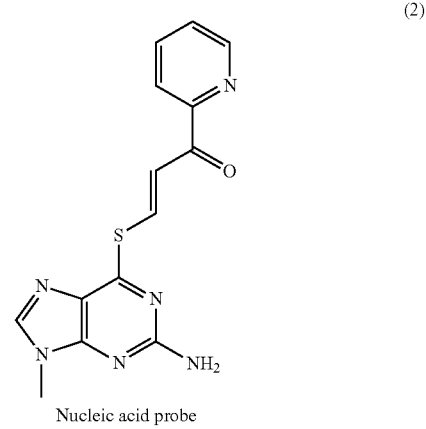

(2)

Nucleic acid probe

In cases where an adenine in the nucleic acid to be labeled is selectively labeled, the reactive nucleobase derivative incorporated into the nucleic acid probe is, for example, (E)-3-(1-(pyridin-2-yl)prop-2-en-1-one)-4-thiothymine (derivative 3) represented by the structural formula (3).

[Chem 3]

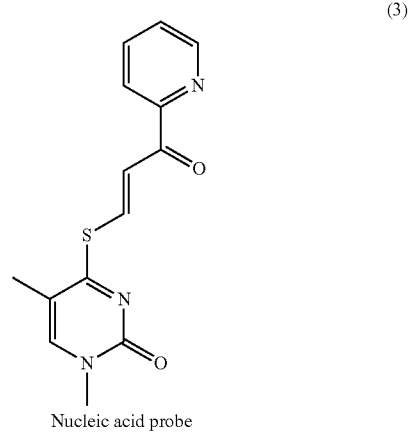

(3)

Nucleic acid probe

For the hybridization of the nucleic acid to be labeled with the nucleic acid probe, the nucleic acid to be labeled and the nucleic acid probe should be mixed together, for example, in a neutral or basic buffer solution. Once the nucleic acid probe is hybridized to the nucleic acid to be labeled, a transfer group contained in the reactive nucleobase derivative is transferred by means of proximity effect to the nucleotide residue containing the target nucleobase in the nucleic acid to be labeled (in the transferring step).

The transferring step should be conducted at 35 to 40° C., preferably at 37° C. The time required for the reaction between the nucleic acid to be labeled and the nucleic acid probe in the reaction and transferring steps is 5 minutes to 6 hours, 10 minutes to 4 hours, or 1 to 3 hours, and is preferably 2 hours, in total.

The transfer group is not particularly limited, provided that the transfer group is reactive. Preferably, the transfer group contains an α,β-unsaturated carbonyl group. In cases where the target nucleobase is a guanine nucleobase, the transfer group is preferably a diketo transfer group. In cases where the derivative 1 is used, a diketo transfer group is transferred to the 2-amino group of guanine under basic conditions.

[Chem 4]

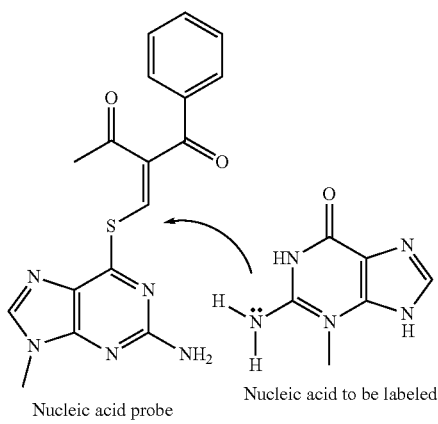

The selectivity of a nucleobase to which a transfer group is transferred can be altered depending on the reaction conditions during the transferring step. Under neutral conditions, a transfer group is transferred to the 4-amino group of cytosine by the derivative 1, as indicated below.

[Chem 5]

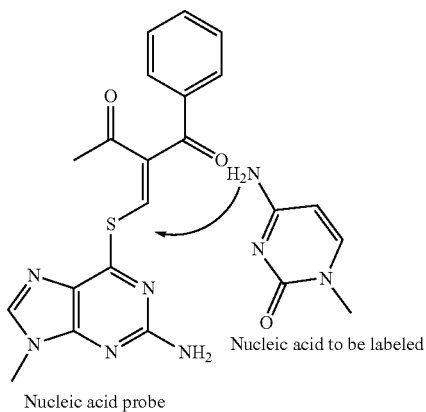

In cases where the target nucleobase is a cytosine nucleobase or an adenine nucleobase, the transfer group is preferably a pyridinyl-keto transfer group. In cases where the derivative 2 is used, a transfer group is transferred to the 4-amino group of cytosine, as indicated below.

[Chem 6]

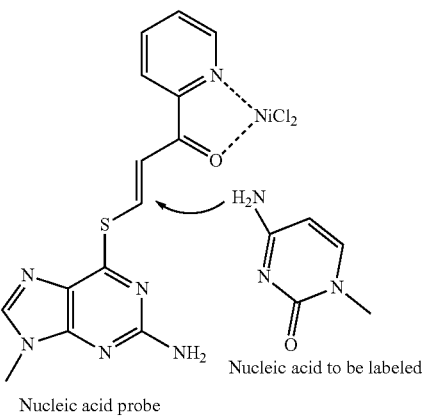

In addition, in cases where the derivative 3 is used, a transfer group is transferred to the 6-amino group of adenine, as indicated below.

[Chem 7]

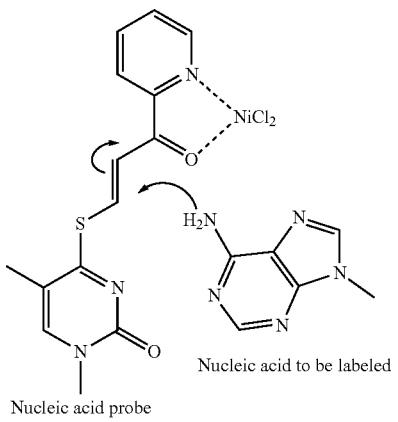

While a transfer group can be transferred to a nucleobase in the nucleic acid to be labeled by using any of the above derivatives 1 to 3, a transfer group can also be transferred to a sugar in the nucleic acid to be labeled. In the latter case, for example, N-(1-acetyl-4-pyridyl)-2-carboxamide-6-aminopurine (derivative 4) represented by the structural formula (4) may be used as a reactive nucleobase derivative incorporated into the nucleic acid probe.

[Chem 8]

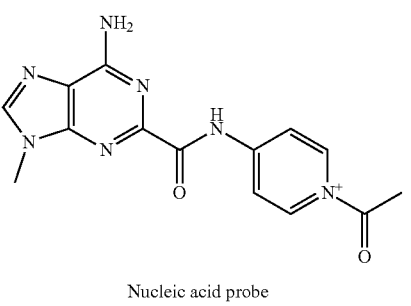

(4)

Use of the derivative 4 results in transfer of acetyl group to the 2' position of the ribose of a nucleotide residue containing an uracil nucleobase as the target nucleobase via the transferring step. Consequently, the OH group at the 2' position of the ribose of the uridine nucleotide is acetylated.

[Chem 9]

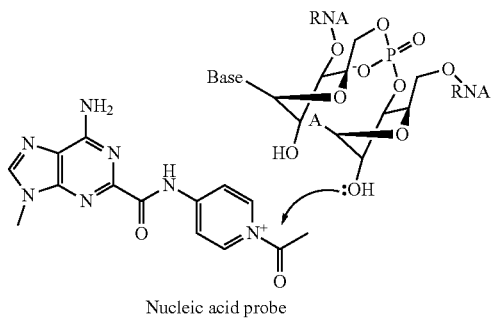

Nucleic acid probe

The above nucleic acid probe can be synthesized, for example, by any known technique using an automated DNA synthesizer. In cases where a nucleic acid probe containing the derivative 1 is synthesized, for example, 2-chloromethylene-1-(pyridin-2-yl)butane-1,3-dione may be allowed to react with an oligonucleotide comprising 2'-deoxyribonucleotides including a 6-thio-2'-deoxyguanosine in a buffer solution.

In cases where a nucleic acid probe containing the derivative 2 is synthesized, for example, (E)-3-iodo-1-(pyridin-2-yl)prop-2-en-1-one may be allowed to react with an oligonucleotide comprising 2'-deoxyribonucleotides including a 6-thio-2'-deoxyguanosine in a buffer solution.

In cases where a nucleic acid probe containing the derivative 3 is synthesized, for example, (E)-3-iodo-1-(pyridin-2-yl)prop-2-en-1-one may be allowed to react with an oligonucleotide comprising 2'-deoxyribonucleotides including a 4-thiothymidine in a buffer solution.

In cases where a nucleic acid probe containing the derivative 4 is synthesized, for example, acetic anhydride may be allowed to react with an oligonucleotide comprising 2'-deoxyribonucleotides including an N-(1-acetyl-4-pyridyl)-2-carboxamide-6-aminopurine in a buffer solution. A method of synthesizing the derivative 4 will be illustrated in Example 3 below.

The length of the nucleic acid probe is not particularly limited, provided that a duplex formed between the nucleic acid probe and target RNA is stably maintained. The length of the nucleic acid probe may be longer or shorter than that of the nucleic acid to be labeled. The length of the nucleic acid probe is, for example, 10 to 20 nucleotides, 12 to 18 nucleotides, or 13 to 17 nucleotides. The incorporated reactive nucleobase derivative in the nucleic acid probe is, for example, not preferably located at the 3' or 5' end of the oligonucleotide chain with a length of 10 to 20 nucleotides, but preferably located 5 to 10 nucleotides or 6 to 8 nucleotides inside of the 3' or 5' end.

In the labeling step, the transfer group transferred to the nucleotide residue is labeled with a radioactive material. Any known radioactive material may be used for the labeling. The radioactive material is, for example, tritium. The above transfer group can be labeled with tritium by reaction between the nucleic acid to be labeled and tritium-labeled sodium borohydride in water.

For example, a transfer group transferred to the nucleic acid to be labeled and originally contained in the derivative 1 can be labeled with tritium, as indicated below.

[Chem 10]

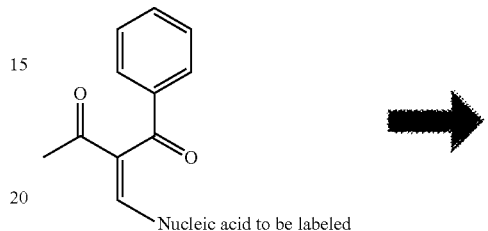

Nucleic acid to be labeled

Nucleic acid to be labeled

Transfer groups transferred to the nucleic acid to be labeled and originally contained in the derivatives 2 and 3 can be labeled with tritium, as indicated below.

[Chem 11]

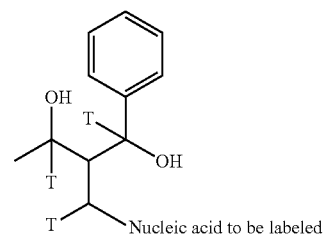

Nucleic acid to be labeled

Nucleic acid to be labeled

A transfer group transferred to the nucleic acid to be labeled and originally contained in the derivative 4 can be labeled with tritium, as indicated below.

[Chem 12]

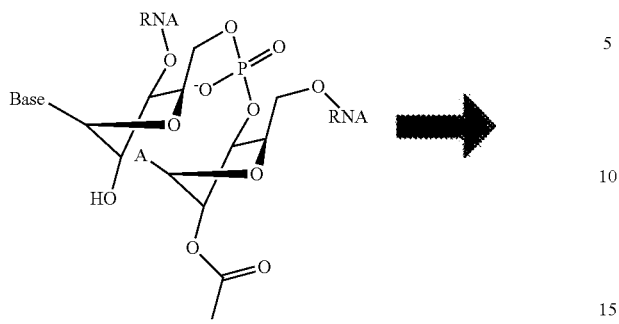

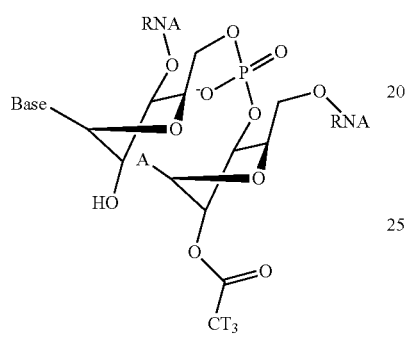

In addition to tritium, examples of the radioactive material include radioisotopes such as $^{18}F$, $^{131}I$, $^{76}Br$, $^{67}Ga$, $^{68}Ga$, $^{99m}Tc$, $^{111}In$, $^{89}Sr$, $^{186}Re$, $^{153}Sm$, and $^{117m}Sn$. For the labeling with a radioisotope, for example, a transfer group containing an alkyne moiety should be transferred to a nucleotide residue, followed by a click reaction between an azide compound containing a radioisotope (a radiolabeling unit) and the alkyne. The click reaction between the alkyne and the azide compound is a [3+2]-cycloaddition (Huisgen cycloaddition) between the alkyne and the azide compound. A 1,2,3-triazole derivative is obtained by the Huisgen cycloaddition. Conditions for the Huisgen cycloaddition can be appropriately selected.

[Chem 13]

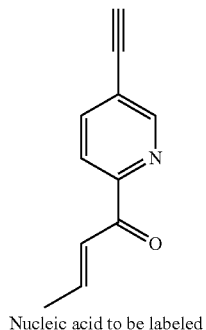

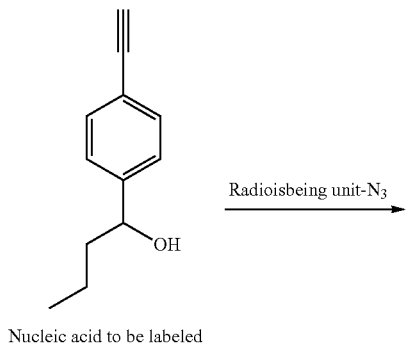

In addition to the above click reaction, esterification/amidation of a reduced transfer group with a haloacetate as a radiolabeling unit as indicated below can result in incorporation of a radioisotope such as $^{18}F$, $^{131}I$, and $^{76}Br$. Conditions for the esterification can be appropriately selected.

[Chem 14]

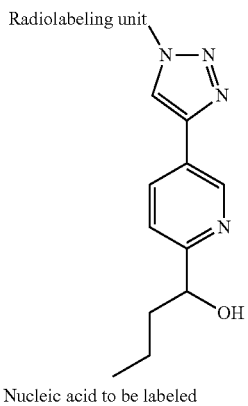

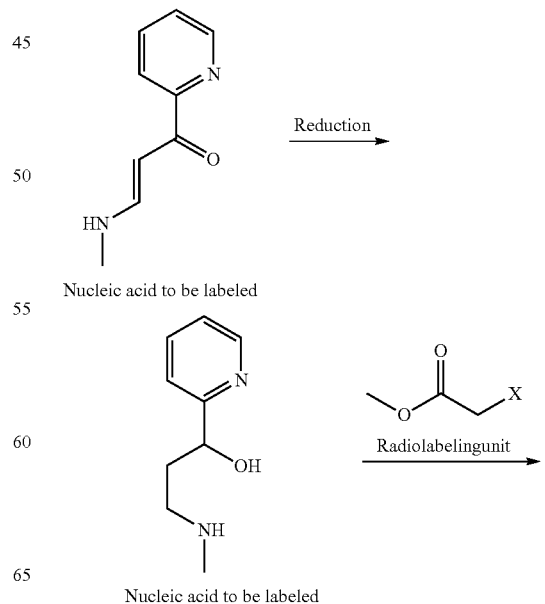

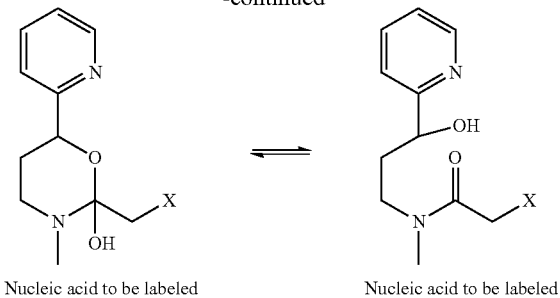

Nucleic acid to be labeled      Nucleic acid to be labeled

As described in detail above, in the labeling method for nucleic acid according to the present embodiment, a nucleic acid probe that contains a reactive nucleobase derivative incorporated at a position complementary to that of a target nucleobase as a target of labeling in a nucleic acid to be labeled is hybridized to the nucleic acid to be labeled and a transfer group is then transferred to the nucleic acid to be labeled. Thus, the nucleic acid, whether of synthetic or natural origin, can be chemically modified with the transfer group at a desired position on the nucleic acid in a selective manner depending on the nucleotide sequence of the nucleic acid probe. Because a nucleic acid to be labeled can be labeled at any position on the nucleic acid other than both the ends by the present labeling method for nucleic acid, this method is suitable for monitoring the behavior of a nucleic acid, such as siRNA, which is susceptible to in vivo fragmentation.

Furthermore, in the labeling method for nucleic acid according to the present embodiment, the transfer group is labeled with a radioactive material, so that the nucleic acid to be labeled can be labeled in such a manner that the labeled nucleic acid can be sensitively detected. The transfer group according to the present embodiment is not as sterically bulky as the aforementioned metal complex and does not compromise the function of the nucleic acid, as shown in Text Example 2 below.

In cases where a double-stranded nucleic acid is used as the nucleic acid to be labeled, the labeling method for nucleic acid according to the present embodiment may include the step of separating the double-stranded nucleic acid into single strands prior to the above reaction step.

Additionally, because the labeling method for nucleic acid according to the present embodiment allows a nucleic acid to be chemically modified with a transfer group at a desired position on the nucleic acid in a selective manner, the present labeling method can produce a nucleic acid labeled at different positions on the same nucleic acid to be labeled. In this case, the labeling method for nucleic acid further includes the following first to third steps, in addition to the above reaction, transferring, and labeling steps.

In the first step, a nucleic acid probe that has a nucleotide sequence complementary to that of the nucleic acid to be labeled and contains a reactive nucleobase derivative incorporated at a position complementary to that of a nucleobase (designated as the nucleobase Y) different from the position of the target nucleobase (designated as the nucleobase X) in the nucleic acid to be labeled is hybridized to the nucleic acid to be labeled. In the second step, a transfer group contained in the reactive nucleobase derivative of the nucleic acid probe, which is hybridized in the first step to the nucleic acid to be labeled, is transferred to the nucleotide residue containing the nucleobase Y in the nucleic acid to be labeled. In the third step, the transfer group transferred to the nucleotide residue containing the nucleobase Y is labeled with a radioactive material different from the radioactive material used in the labeling step.

Thus, for example, a fragment containing the nucleobase X and another fragment containing the nucleobase Y can be distinguishably detected even when the nucleic acid to be labeled is degraded in vivo. Consequently, the behavior of multiple fragments derived from the nucleic acid to be labeled can be monitored, and the obtained information on the multiple fragments can be totally analyzed to elucidate the behavior of the nucleic acid to be labeled.

In another embodiment, a method for nucleic acid preparation is provided. The method for nucleic acid preparation includes the step of mixing a first nucleic acid to be labeled that was obtained in the above labeling step and containing a labeled nucleotide residue that contains a nucleobase X and a second nucleic acid to be labeled that was obtained in the above third step and containing a labeled nucleotide residue that contains a nucleobase Y. Once a nucleic acid sample containing the first and second nucleic acids to be labeled that was obtained by the method for nucleic acid preparation is introduced into the body, the behavior of the nucleic acid to be labeled can be elucidated in detail. The number of labeled positions in a set of nucleic acids to be labeled is not limited to two but may be three or more.

EXAMPLES

The present disclosure will be more specifically described by the following Examples, but the present disclosure is not limited thereto.

Example 1: Tritium Labeling of Cytosine in Single-Stranded RNA

RNA 01 as a nucleic acid to be labeled is the sense strand of a siRNA against the (P)RR/ATP6AP2 gene. The nucleotide sequence of RNA 01 is represented by SEQ ID NO: 1. A synthetic DNA fragment that was complementary to a region extending between the A residue at four nucleotides and the G residue at 20 nucleotides downstream of the 5' end of RNA 01 was designated as nucleic acid probe 01. The nucleotide sequence of nucleic acid probe 01 is represented by SEQ ID NO: 2. Nucleic acid probe 01 contains a 6-thio-2'-deoxyguanosine residue at the eighth position from the 5' end, which is complementary to the position of the C residue at 13 nucleotides downstream of the 5' end of RNA 01.

A mixture of nucleic acid probe 01 (50 µM) and a pyridinyl-keto transfer group-containing compound ((E)-3-iodo-1-(pyridin-2-yl)prop-2-en-1-one, 750 µM) was prepared in a carbonate buffer (25 mM, pH 10.0) at 0° C. and allowed to react at the same temperature for 30 minutes to obtain artificial nucleic acid 01 containing a reactive nucleobase derivative.

To the above reaction solution, 1 M NaCl in HEPES buffer (0.5 M HEPES, pH 7.0) and ultra-pure water were added to dilute the original reaction solution three times. This solution was heated at 65° C. for 3 minutes and then rapidly cooled down at 0° C. To the solution, RNA 01, $NiCl_2$, and ultra-pure water were added at 0° C. to obtain the following final concentrations. The solution was incubated at 37° C. for 2 hours. Thus, modified RNA 01 comprising the transfer group transferred to RNA 01 was obtained.

| | |
|---|---|
| RNA 01 | 5 µM |
| NiCl$_2$ | 75 µM |
| Artificial nucleic acid 01 | 7.5 µM |
| HEPES buffer | 50 mM (pH 7.0) |
| NaCl | 100 mM |

The obtained reaction solution was concentrated, and a carbonate buffer, NaBT$_4$, and ultra-pure water were added to the resulting reaction solution to obtain the following final concentrations.

NaBT$_4$ (3.8 mM, 3.7 GBq/mmol)
Modified RNA 01 (25 µM)
Carbonate buffer (25 mM, pH 10.0)

The reaction in the above reaction solution was allowed to proceed at room temperature for 30 minutes, and the reaction solution was then neutralized by adding 10% acetic acid in water. The resulting crude reaction product was purified by HPLC (column: 4.6×250 mm, manufactured by Osaka Soda Co., Ltd.; flow rate: 1.0 ml/min; buffer A: TEAA, buffer B: CH$_3$CN, linear-gradient from 10% B to 15% B in 20 min; UV detector at 254 nm), and fractions corresponding to individual UV peaks were collected. A volume of 10 µl from the fraction corresponding each UV peak was diluted 100 times in scintillation cocktail (Ultima Gold MV), and the radioactivity was then measured on a liquid scintillation counter. The collected HPLC fractions were lyophilized, and then reconstituted in PBS and stored frozen.

In contrast, RNA 02, which is the antisense strand of a siRNA against the (P)RR/ATP6AP2 gene, was designated as a nucleic acid to be labeled and was labeled with tritium in the same manner as RNA 01. The nucleotide sequence of RNA 02 is represented by SEQ ID NO: 3. A synthetic DNA fragment that was complementary to a region extending between the A residue at seven nucleotides and the A residue at 21 nucleotides downstream of the 5' end of RNA 02 was designated as nucleic acid probe 02. The nucleotide sequence of nucleic acid probe 02 is represented by SEQ ID NO: 4. Nucleic acid probe 02 contains a 6-thio-2'-deoxyguanosine residue at the 11th position from the 5' end, which is complementary to the position of the C residue at 12 nucleotides downstream of the 5' end of RNA 02. The reaction between nucleic acid probe 02 and a pyridinyl-keto transfer group-containing compound ((E)-3-iodo-1-(pyridin-2-yl)prop-2-en-1-one) was allowed to proceed in the same manner as nucleic acid probe 01 to obtain artificial nucleic acid 02 containing a reactive nucleobase derivative.

As in the case of RNA 01, modified RNA 02 obtained from the reaction between RNA 02 and artificial nucleic acid 02 and comprising the transfer group transferred to RNA 02 was allowed to react with NaBT$_4$, and the resulting crude reaction product was purified by HPLC, and the radioactivity was measured in collected fractions corresponding to individual UV peaks. The collected HPLC fractions were lyophilized, and then reconstituted in PBS and stored frozen.

(Result)

Figure 1B:
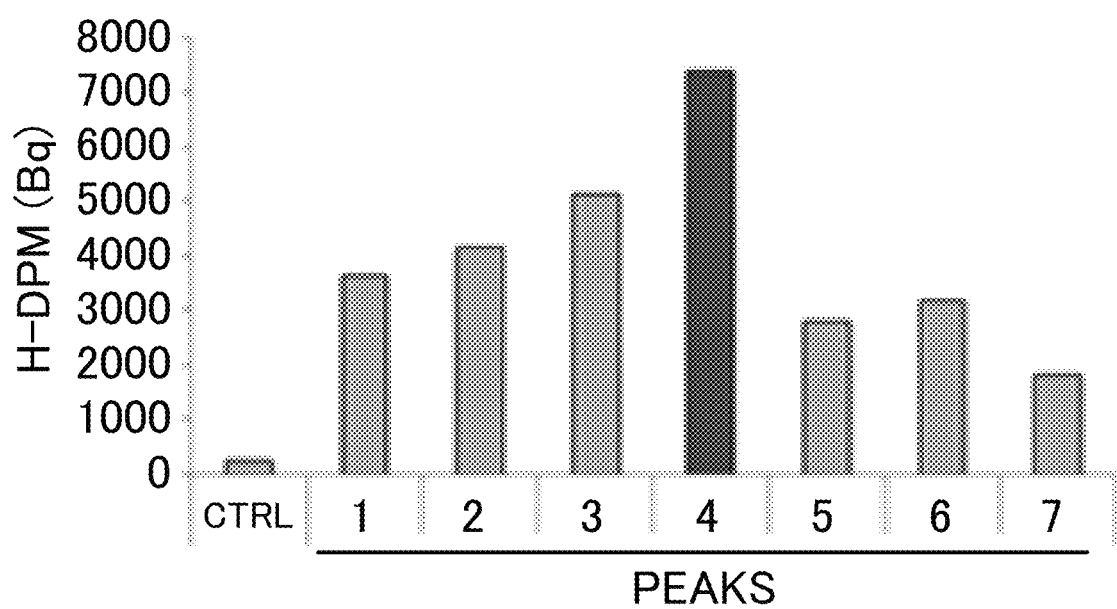
FIG. 1B shows the result of purification of the labeled sense strand of a siRNA according to Example 1 by HPLC, in which radiation doses corresponding to individual UV peaks are illustrated.

FIG. 1A shows the UV peaks corresponding to crude reaction products obtained from modified RNA 01, while FIG. 1B shows the radiation doses corresponding to the individual UV peaks. A tritium-labeled species of RNA 01 ($^3$H-RNA 01) was successfully obtained from the isolated and purified fraction corresponding to the peak 4.

Figure 2A:
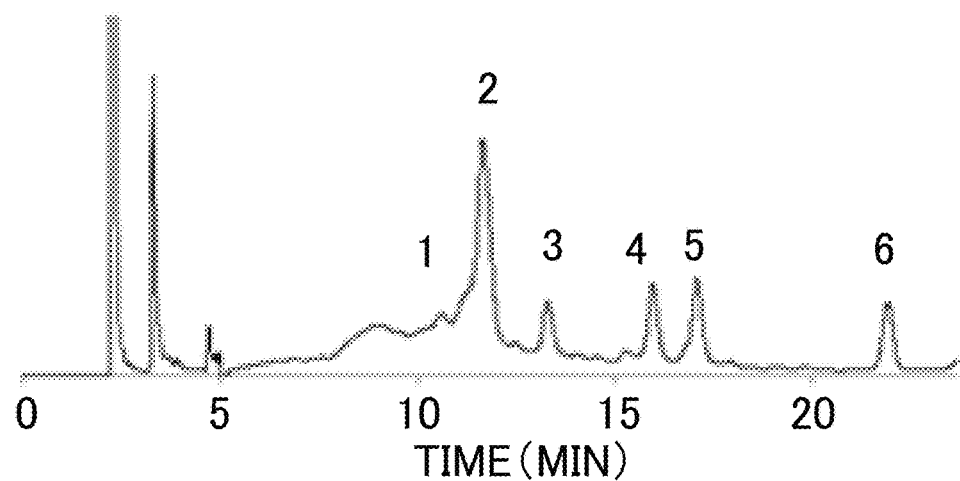
FIG. 2A shows the result of purification of the labeled antisense strand of a siRNA according to Example 1 by HPLC, in which the UV peaks corresponding to crude reaction products are illustrated.
Figure 2B:
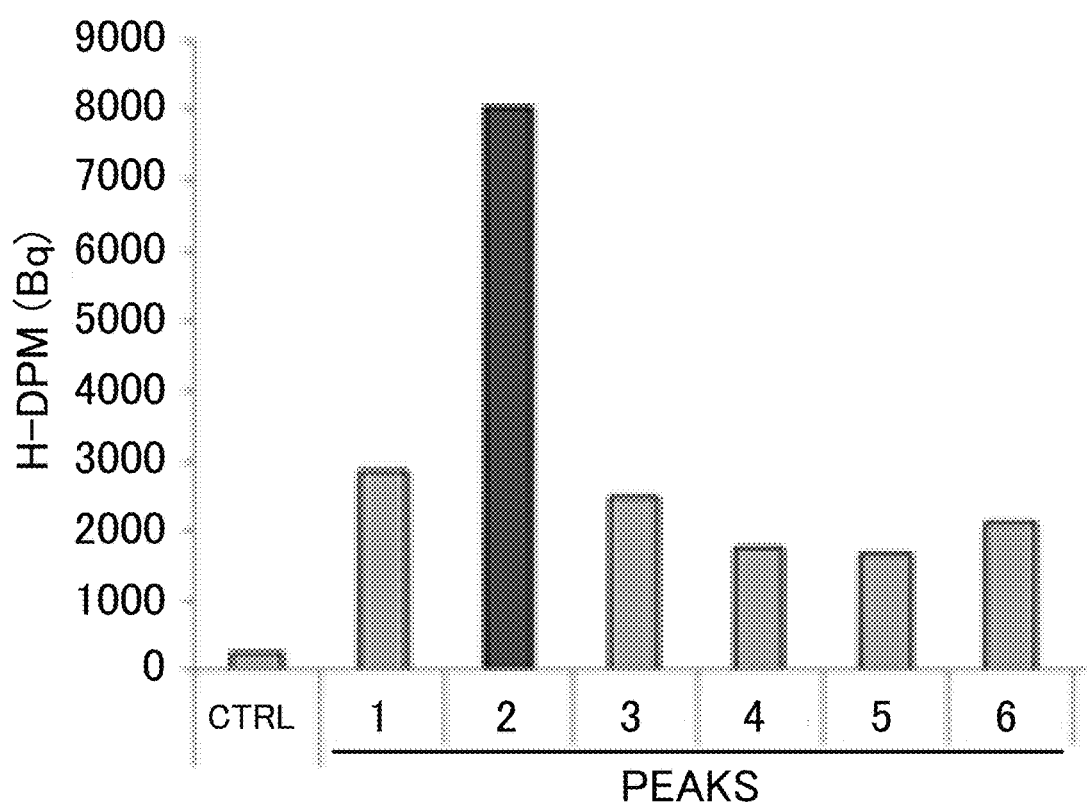
FIG. 2B shows the result of purification of the labeled antisense strand of a siRNA according to Example 1 by HPLC, in which the radiation doses corresponding to individual UV peaks are illustrated.

FIG. 2A shows the UV peaks corresponding to crude reaction products obtained from modified RNA 02, while FIG. 2B shows the radiation doses corresponding to the individual UV peaks. A tritium-labeled species of RNA 02 ($^3$H-RNA 02) was successfully obtained from the isolated and purified fraction corresponding to the peak 2.

Test Example 1: Analysis of Tritium-Labeled RNA Behavior in Mouse Eyeball

BALB/c mice (male) were reared for one week before a simple medium (PBS), $^3$H-RNA 01, $^3$H-RNA 02, or a siRNA prepared from $^3$H-RNA 02 and an unlabeled species of RNA 01 was administered intravitreally to the mice via the sclera of the corneal limbus with a microsyringe and a 33G needle under sevoflurane inhalation anesthesia. The $^3$H-RNA 01, $^3$H-RNA 02, and siRNA were administered at a concentration of 100 pmol/eye. After 5 minutes, 10 minutes, 30 minutes, 1 hour, and 3 hours of administration, the mice were euthanized by cervical dislocation to extract one eyeball, or eye tissues including the segment containing the lens and vitreous humor and the segment containing the retina from each euthanized mouse. Four mice were used for each treatment time. To one eyeball or each eye tissue, 0.5 ml of Solvable (manufactured by PerkinElmer Inc.) was added, and the resulting mixture was incubated overnight at 50° C. to dissolve the biological material. After the biological material was completely dissolved, the mixture was cooled down to normal temperature, to which 10 ml of Ultima Gold MV was then added to measure the radioactivity on a liquid scintillation counter. The radioactivity was calculated and expressed in becquerels per gram of organ.

(Result)

Figure 3:
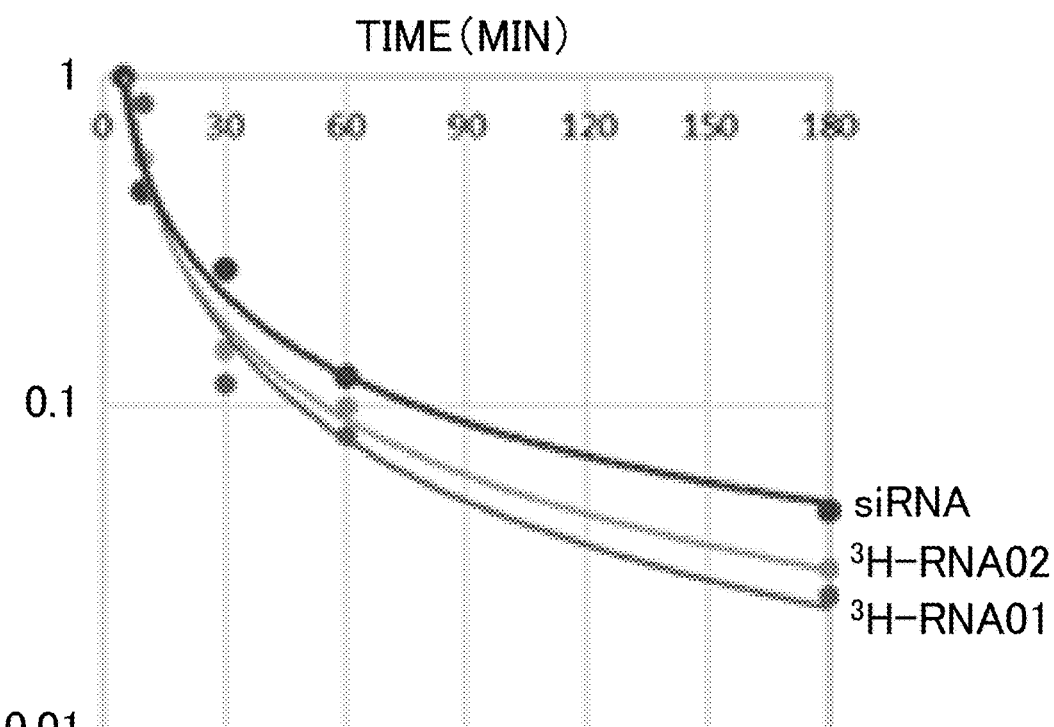
FIG. 3 shows the rate of decrease in radiation dose in eyeball according to Test Example 1.

FIG. 3 shows the rate of decrease in radiation dose in eyeball relative to that at 5 minutes after administration of each of the $^3$H-RNA 01, $^3$H-RNA 02, and siRNA. It was indicated that the double-stranded siRNA had a longer residence time in eyeball than the single-stranded $^3$H-RNA 01 and $^3$H-RNA 02.

Figure 4:
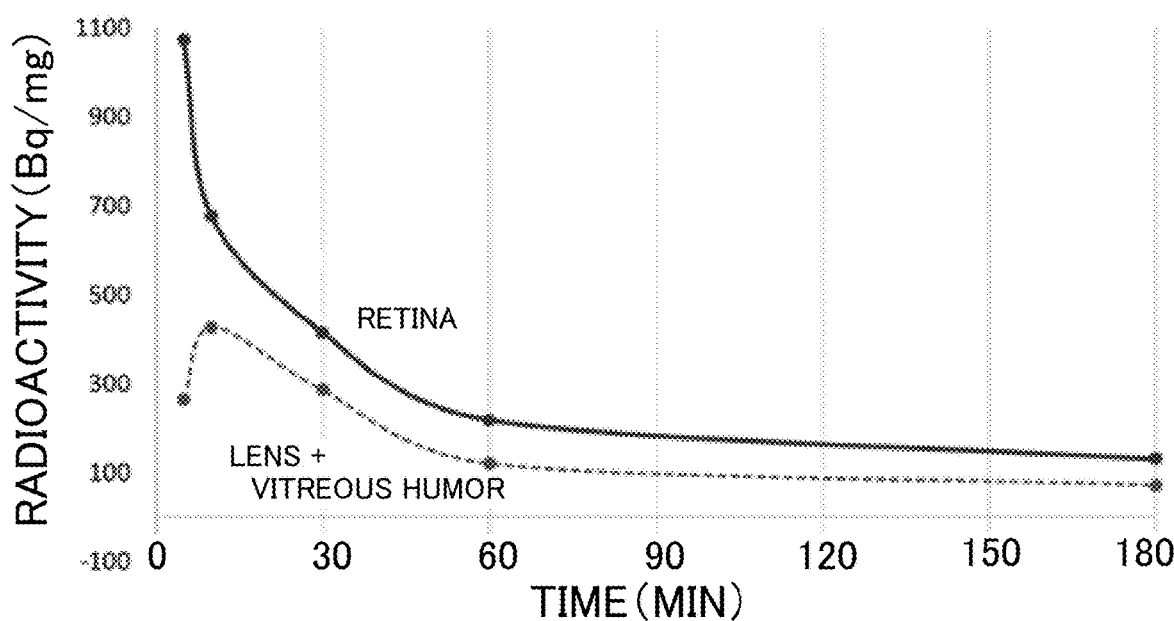
FIG. 4 shows the change in radioactivity over time in each mouse eye tissue according to Test Example 1.

FIG. 4 shows the change in radioactivity over time in each mouse eye tissue extracted from mice administered with the siRNA. The change in radioactivity over time in either the segment containing the retina or the segment containing the lens and vitreous humor was successfully tracked. It was indicated that the behavior of the siRNA in the segment containing the retina was different from that in the segment containing the lens and vitreous humor.

Example 2: Tritium Labeling of Cytosine in Synthetic mRNA

A synthetic mRNA encoding a peptide with an amino acid sequence represented by SEQ ID NO: 5 (molecular weight (MW): 2897.4872; MW of a protonated species: 2898.2231) for cell-free translation systems was designated as a nucleic acid to be labeled and was labeled with tritium in the same manner as RNA 01. The nucleotide sequence of the synthetic mRNA is represented by SEQ ID NO: 6. A synthetic DNA fragment that was complementary to a region extending between the A residue at 82 nucleotides and the A residue at 92 nucleotides downstream of the 5' end of the synthetic mRNA was designated as nucleic acid probe 03. Nucleic acid probe 03 is a synthetic nucleic acid comprising 3'-OMe-modified ribonucleotides. The nucleotide sequence of nucleic acid probe 03 is represented by SEQ ID NO: 7. The theoretical and observed masses of nucleic acid probe 03 were found to be 3596.59 and 3596.53 by MALDI/TOF MS, respectively. Nucleic acid probe 03 contains a 6-thio-2'-deoxyguanosine residue at the seventh position from the 5' end, which is complementary to the position of the C residue at 88 nucleotides downstream of the 5' end of the synthetic mRNA. The reaction between nucleic acid probe 03 and a pyridinyl-keto transfer group-containing compound ((E)-3-iodo-1-(pyridin-2-yl)prop-2-en-1-one) was allowed to proceed in the same manner as nucleic acid probe 01 to obtain artificial nucleic acid 03 containing a reactive nucleobase derivative. The theoretical and observed masses of artificial nucleic acid 03 were found to be 3727.63 and 3727.73 by MALDI/TOF MS, respectively.

The reaction for transferring the transfer group to the synthetic mRNA was performed by incubating the synthetic mRNA and artificial nucleic acid 03 in HEPES buffer, pH 7.0, at 37° C. for 1 hour in the presence of 75 μM $NiCl_2$. Next, the reduction was allowed to proceed in the presence of $NaBT_4$, and low molecular weight impurities were then removed by centrifugal filtration (Amicon Ultra-0.5 mL 10K, manufactured by Merck KGaA) to purify crude reaction products by HPLC. The HPLC elution conditions were changed to conditions using buffer A: TEAA, buffer B: $CH_3CN$, and a linear-gradient from 10% B to 20% B in 20 min. The radioactivity was measured in collected fractions corresponding to individual UV peaks. The collected HPLC fractions were lyophilized, and then reconstituted in PBS and stored frozen.

(Result)

Figure 5A:
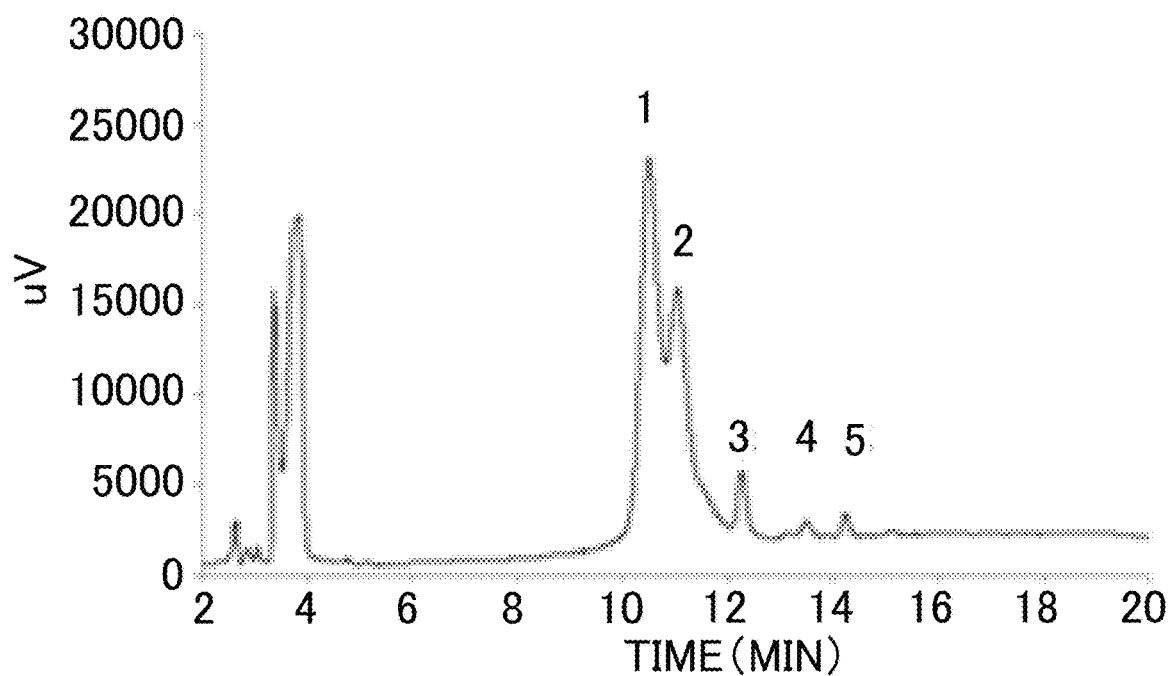
FIG. 5A shows the result of purification of a labeled synthetic mRNA according to Example 2 by HPLC, in which UV peaks corresponding to crude reaction products are illustrated.
Figure 5B:
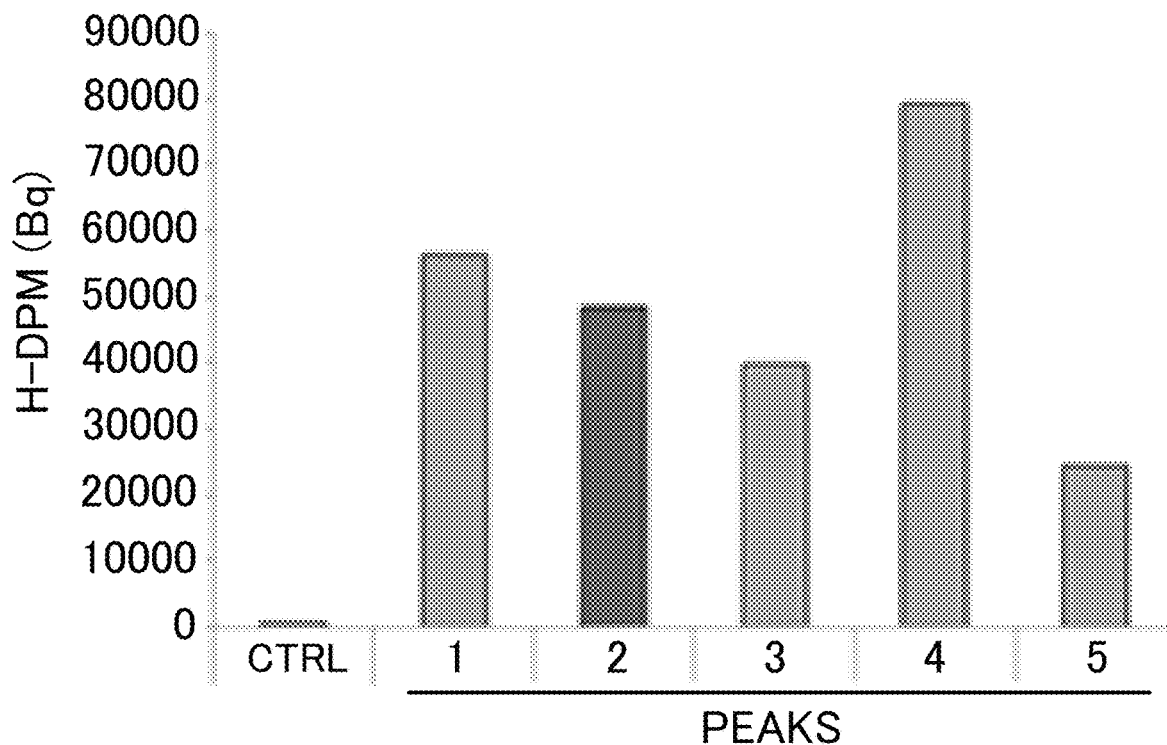
FIG. 5B shows the result of purification of a labeled synthetic mRNA according to Example 2 by HPLC, in which the radiation doses corresponding to individual UV peaks are illustrated.

FIG. 5A shows the UV peaks corresponding to crude reaction products, while FIG. 5B shows the radiation doses corresponding to the individual UV peaks. A tritium-labeled species of RNA 03 ($^3$H-RNA 03) was successfully obtained from the isolated and purified fraction corresponding to the peak 2.

Test Example 2: Analysis of Effects of Nonradioactively Labeled RNA on Translation A nonradioactively labeled species of RNA 03, which was prepared in the same manner as the above tritium-labeled species of RNA 03 except that $NaBH_4$ was used instead of $NaBT_4$, was added to a translation system using a Pure system (Pure Frex 2.0, manufactured by GeneFrontier Co.) and was allowed to react at 37° C. for 1 hour. The reaction solution was then subjected to affinity chromatography using anti-T7-tag agarose beads, and the molecular weight of the product in the obtained elute was analyzed by mass spectrometry (MALDI-TOF MASS).

(Result)

Figure 6:
FIG. 6 shows the result of mass spectrometric analysis according to Test Example 2.
Figure 6:
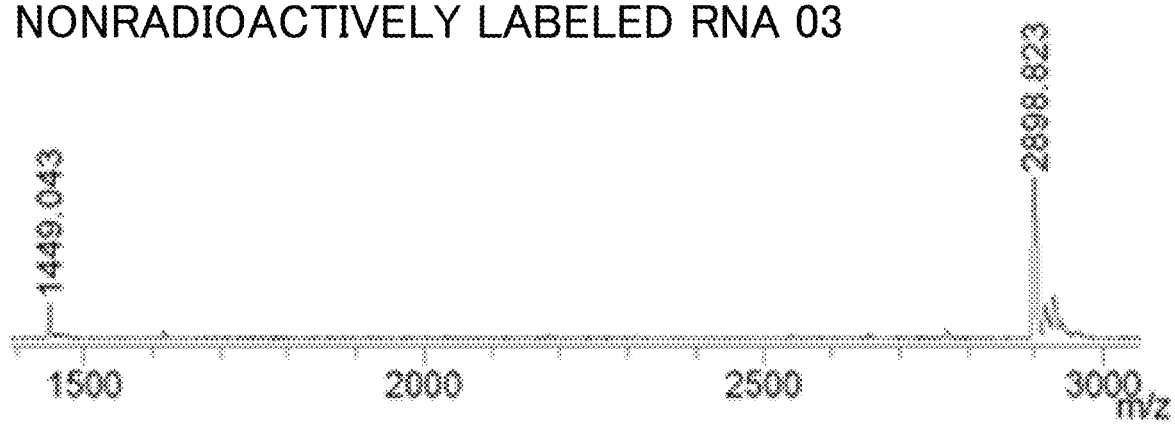

FIG. 6 shows the spectra obtained from the mass spectrometric analysis. The accurate molecular weight of the synthesized peptide was expected to be 2898.22, and the result of the analysis indicated that the same peptide was produced from the nonradioactively labeled species of RNA 03 and an unmodified species of the mRNA. Additionally, in an experiment using an artificial nucleic acid complementary to a region extending between the A residue at 86 nucleotides and the A residue at 92 nucleotides downstream of the 5' end of the synthetic mRNA and containing a 6-thio-2'-deoxyguanosine at the fifth position from the 5' end, which is complementary to the position of the C residue at 86 nucleotides downstream of the 5' end of the synthetic mRNA, it was indicated that the same peptide was produced from a nonradioactively labeled species of the mRNA and the unmodified species of the mRNA. Similarly, in an experiment using an artificial nucleic acid complementary to a region extending between the A residue at 70 nucleotides and the C residue at 83 nucleotides downstream of the 5' end of the synthetic mRNA and containing a 6-thio-2'-deoxyguanosine at the 12th position from the 5' end, which is complementary to the position of the C residue at 82 nucleotides downstream of the 5' end of the synthetic mRNA, it was indicated that the same peptide was produced from the nonradioactively labeled species of the mRNA and from the unmodified species of the mRNA. This Test Example indicated that modification of the 4-amino group of cytosine by a pyridine derivative has no effects on translation.

Example 3: Synthesis of the Derivative 4

Precursors of the derivative 4 were synthesized from 2'-deoxyguanosine by the following steps a to j.

[Chem 15]

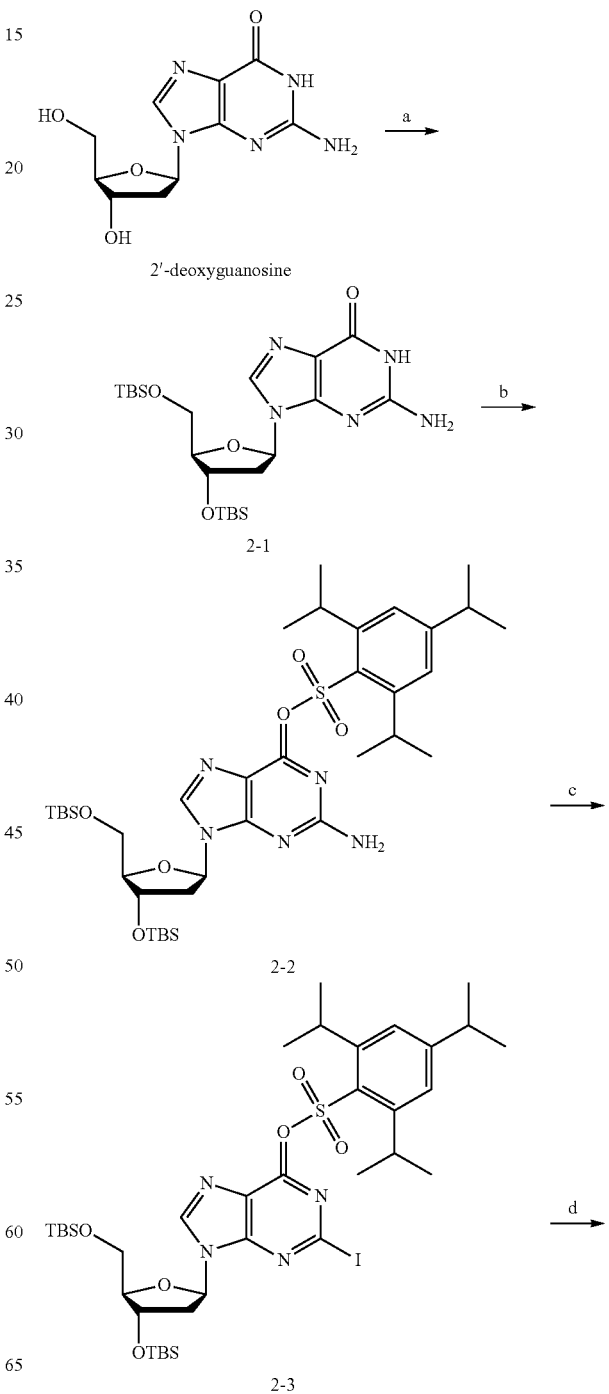

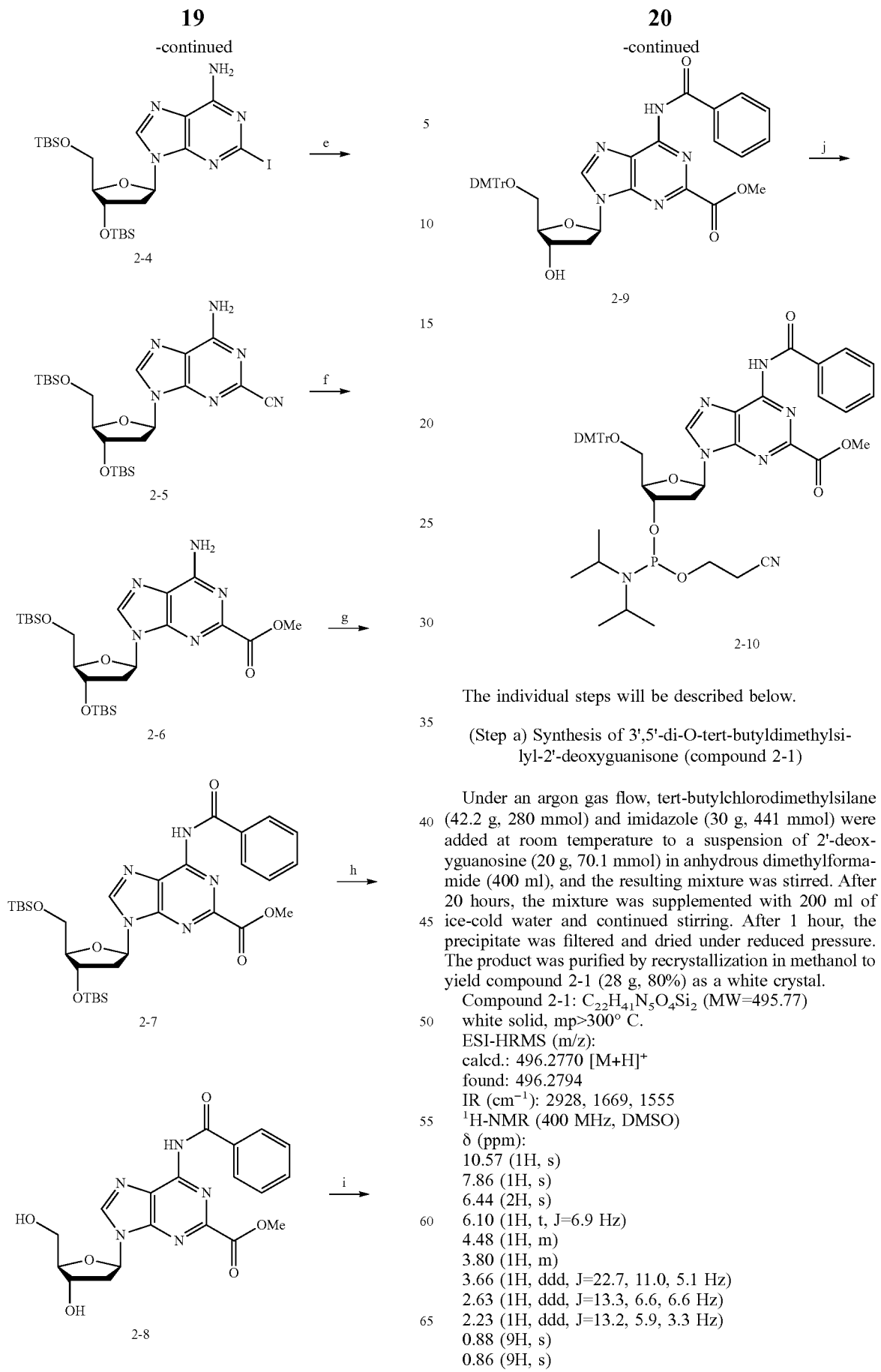

The individual steps will be described below.

(Step a) Synthesis of 3',5'-di-O-tert-butyldimethylsilyl-2'-deoxyguanisone (compound 2-1)

Under an argon gas flow, tert-butylchlorodimethylsilane (42.2 g, 280 mmol) and imidazole (30 g, 441 mmol) were added at room temperature to a suspension of 2'-deoxyguanosine (20 g, 70.1 mmol) in anhydrous dimethylformamide (400 ml), and the resulting mixture was stirred. After 20 hours, the mixture was supplemented with 200 ml of ice-cold water and continued stirring. After 1 hour, the precipitate was filtered and dried under reduced pressure. The product was purified by recrystallization in methanol to yield compound 2-1 (28 g, 80%) as a white crystal.

Compound 2-1: $C_{22}H_{41}N_5O_4Si_2$ (MW=495.77)
white solid, mp>300° C.
ESI-HRMS (m/z):
calcd.: 496.2770 $[M+H]^+$
found: 496.2794
IR ($cm^{-1}$): 2928, 1669, 1555
$^1$H-NMR (400 MHz, DMSO)
δ (ppm):
10.57 (1H, s)
7.86 (1H, s)
6.44 (2H, s)
6.10 (1H, t, J=6.9 Hz)
4.48 (1H, m)
3.80 (1H, m)
3.66 (1H, ddd, J=22.7, 11.0, 5.1 Hz)
2.63 (1H, ddd, J=13.3, 6.6, 6.6 Hz)
2.23 (1H, ddd, J=13.2, 5.9, 3.3 Hz)
0.88 (9H, s)
0.86 (9H, s)

0.09 (6H, s)
0.033 (3H, s)
0.028 (3H, s)

(Step b) Synthesis of 2-amino-9-{(2R,4S,5R)-4-(tert-butyldimethylsilyloxy)-5-[(tert-butyldimethylsilyloxy)methyl]tetrahydrofuran-2-yl}-9H-purine-6-yl-2,4,6-triisopropylbenzenesulfonate (compound 2-2)

A suspension of compound 2-1 (1.0 g, 2.02 mmol) in anhydrous dichloromethane (40 ml) was subjected to azeotropic distillation with anhydrous acetonitrile, and triisopropylbenzenesulfonyl chloride (1.2 g, 3.96 mmol), N,N-dimethyl-4-aminopyridine (25 mg, 0.21 mmol), and triethylamine (560 µl, 4.02 mmol) were added to the suspension under an argon gas flow at 0° C., and the resulting mixture was stirred. After 27 hours, the reaction solution was washed with water and saturated brine, dried on anhydrous sodium sulfate, and then subjected to solvent evaporation under reduced pressure. The residue was purified by silica gel chromatography (hexane/ethyl acetate=10:1→5:1) to yield compound 2-2 (1.36 g, 89%) as a white foam.
Compound 2-2: $C_{37}H_{63}N_5O_6SSi_2$ (MW=762.17)
white foam
ESI-HRMS (m/z):
calcd.: 762.4110 [M+H]+
found: 762.4147
IR ($cm^{-1}$): 2955, 1634, 1574
$^{13}$C-NMR (125 MHz, CDCl$_3$)
δ (ppm): 158.6, 155.7, 155.3, 154.3, 151.0, 140.1, 131.6, 123.9, 116.9, 88.0, 84.0, 72.2, 63.0,
41.1, 34.5, 29.9, 26.1, 25.9, 24.80, 24.76, 23.7, 18.6, 18.2, −4.5
$^1$H-NMR (500 MHz, CDCl$_3$)
δ (ppm):
7.97 (1H, s)
7.20 (2H, s)
6.29 (1H, dd, J=6.6, 6.6 Hz)
4.86 (2H, s)
4.57 (1H, ddd, J=3.1, 3.1, 5.9 Hz)
4.31 (2H, sept, J=6.7 Hz)
3.97 (1H, ddd, J=3.4, 3.6, 3.6 Hz)
3.80 (1H, dd, J=4.2, 11.2 Hz)
3.74 (1H, dd, J=3.2, 11.2 Hz)
2.91 (1H, sept, J=6.9 Hz)
2.56 (1H, m)
2.34 (1H, ddd, J=3.6, 6.1, 13.1 Hz)
1.28-1.25 (18H, m)
0.91 (9H, s)
0.89 (9H, s)
0.10 (6H, s)
0.07 (3H, s)
0.06 (3H, s)

(Step c) Synthesis of 9-{(2R,4S,5R)-4-(tert-butyldimethylsilyloxy)-5-[(tert-butyldimethylsilyloxy)methyl]tetrahydrofuran-2-yl}-2-iodo-9H-purine-6-yl-2,4,6-triisopropylbenzenesulfonate (compound 2-3)

Under an argon gas flow, copper iodide (322 mg, 1.73 mmol), iodine (732 mg, 5.77 mmol), diiodomethane (700 µl, 7.22 mmol), and isoamyl nitrite (970 µl, 7.22 mmol) were added at room temperature to a suspension of compound 2-2 (1.1 g, 1.44 mmol) in anhydrous acetonitrile (85 ml), and the resulting mixture was stirred at 75° C. After 45 minutes, the reaction solution was cooled down to room temperature and then subjected to solvent evaporation under reduced pressure. The residue was dissolved in chloroform, and the resulting solution was washed with saturated aqueous sodium thiosulfate solution and saturated brine, dried on anhydrous sodium sulfate, and then subjected to solvent evaporation under reduced pressure. The residue was purified by silica gel chromatography (Kanto Chemical Silica Gel 60N, hexane/ethyl acetate=10:1) to yield compound 2-3 (0.874 mg, 69%) as a white foam.
Compound 2-3: $C_{37}H_{61}IN_4O_6SSi_2$ (MW=873.05)
white foam
ESI-HRMS (m/z):
calcd.: 895.2787 [M+Na]+
found: 895.2792
IR ($cm^{-1}$): 2926
$^{13}$C-NMR (125 MHz, CDCl$_3$)
δ (ppm): 154.6, 154.3, 153.4, 151.0, 143.5, 131.4, 124.0, 123.3, 115.7, 88.4, 85.1, 72.0, 62.8, 41.5, 34.5, 30.0, 26.1, 25.9, 25.0, 24.9, 23.71, 23.70, 18.6, 18.2, −4.5, −4.6, −5.2, −5.3
$^1$H-NMR (400 MHz, CDCl$_3$)
δ (ppm):
8.25 (1H, s)
7.20 (2H, s)
6.38 (1H, dd, J=6.4, 6.4 Hz)
4.59 (1H, m)
4.24 (2H, sept, J=6.3 Hz)
3.98 (1H, ddd, J=3.4, 3.4, 3.4 Hz)
3.84 (1H, dd, J=4.0, 11.0 Hz)
3.74 (1H, dd, J=3.4, 11.3 Hz)
2.91 (1H, sept, J=6.9 Hz)
2.58 (1H, m)
2.41 (1H, m)
1.19-1.27 (18H, m)
0.89 (9H, s)
0.88 (9H, s)
0.09 (6H, s)
0.06 (3H, s)
0.06 (3H, s)

(Step d) Synthesis of 6-amino-9-{(2R,4S,5R)-4-(tert-butyldimethylsilyloxy)-5-[(tert-butyldimethylsilyloxy)methyl]tetrahydrofuran-2-yl}-2-iodo-9H-purine (compound 2-4)

To a solution of compound 2-3 (1.0 g, 1.145 mmol) in tetrahydrofuran (13 ml), 28% aqueous ammonia solution (7.0 ml, 8673 mmol) was added, and the resulting mixture was stirred at room temperature. After 69 hours, the reaction solution was diluted with saturated aqueous ammonium chloride solution and extracted with ethyl acetate. The solution was washed with saturated aqueous sodium bicarbonate solution, dried on anhydrous sodium sulfate, and then subjected to solvent evaporation under reduced pressure. The residue was purified by silica gel chromatography (hexane/ethyl acetate=3:1→5:2) to yield compound 2-4 (619 mg, 89%) as a white foam.
Compound 2-4: $C_{22}H_{40}IN_5O_3Si_2$ (MW=605.67)
white foam
ESI-HRMS (m/z):
calcd.: 628.1607 [M+Na]+
found: 628.1614
IR ($cm^{-1}$): 2956, 1649, 1589
$^{13}$C-NMR (125 MHz, CDCl$_3$)
δ (ppm): 155.2, 150.0, 139.5, 120.1, 119.8, 88.1, 84.7, 72.0, 62.9, 41.3, 26.1, 25.9, 18.6, 18.2, −4.5, −4.6, −5.2, −5.3

¹H-NMR (400 MHz, CDCl₃)
δ (ppm):
7.99 (1H, s)
6.33 (1H, dd, J=6.4, 6.4 Hz)
5.61 (2H, s)
4.61 (1H, m)
3.96 (1H, ddd, J=3.8, 3.8, 3.8 Hz)
3.86 (1H, dd, J=4.5, 11.1 Hz)
3.75 (1H, dd, J=3.4, 11.3 Hz)
2.63 (1H, m)
2.38 (1H, ddd, J=4.1, 6.3, 13.3 Hz)
0.90 (9H, s)
0.90 (9H, s)
0.09 (6H, s)
0.08 (6H, s)

(Step e) Synthesis of 6-amino-9-{(2R,4S,5R)-4-(tert-butyldimethylsilyloxy)-5-[(tert-butyldimethylsilyloxy)methyl]tetrahydrofuran-2-yl}-9H-purine-2-carbonitrile (compound 2-5)

To a solution of compound 2-4 (700 mg, 1.156 mmol) in anhydrous dimethylformamide (20 ml), tributyltin cyanide (548 mg, 1.73 mmol) was added at room temperature under an argon gas flow, and the resulting mixture was degassed for 20 minutes. Then, the mixture was supplemented with tetrakis(triphenylphosphine)palladium (160 mg, 0.138 mmol) and stirred with heating at 110° C. After 1 hour, the reaction solution was cooled down to room temperature and then diluted with ethyl acetate, and the resulting solution was washed with saturated aqueous ammonium chloride solution, dried on anhydrous sodium sulfate, and then subjected to solvent evaporation under reduced pressure. The residue was purified by silica gel chromatography (hexane to hexane/ethyl acetate=2:1), and further purified by silica gel chromatography (hexane/ethyl acetate=5:2) to yield compound 2-5 (572 mg, 98%) as a white foam.

Compound 2-5: $C_{23}H_{40}N_6O_3Si_2$ (MW=504.78)
white foam
ESI-HRMS (m/z):
calcd.: 527.2593 [M+Na]⁺
found: 527.2596
IR (cm⁻¹): 2929, 2856, 1656, 1594
¹³C-NMR (125 MHz, CDCl₃)
¹H-NMR (400 MHz, CDCl₃)
δ (ppm):
8.26 (1H, s)
6.37 (1H, dd, J=6.3, 6.3 Hz)
5.69 (2H, s)
4.62 (1H, m)
4.00 (1H, ddd, J=3.7, 3.7, 3.7 Hz)
3.88 (1H, dd, J=4.3, 11.3 Hz)
3.76 (1H, dd, J=3.1, 11.3 Hz)
2.65 (1H, m)
2.44 (1H, m)
0.91 (9H, s)
0.89 (9H, s)
0.10 (3H, s)
0.10 (3H, s)
0.07 (3H, s)
0.07 (3H, s)

(Step f) Synthesis of 6-amino-9-{(2R,4S,5R)-4-(tert-butyldimethylsilyloxy)-5-[(tert-butyldimethylsilyloxy)methyl]tetrahydrofuran-2-yl}-9H-purine-2-methylcarboxylate (compound 2-6)

Under an argon gas flow, 0.5N sodium methoxide solution in methanol (1.0 ml, 0.50 mmol) was added at room temperature to a solution of compound 2-5 (540 mg, 1.07 mmol) in anhydrous methanol (26 ml), and the resulting mixture was stirred. After 28 hours, the reaction solution was neutralized with Dowex 50 (H+) and filtered through celite, and the filtrate was then subjected to solvent evaporation under reduced pressure. The residue was dissolved in methanol, and water (6.5 ml) and then 10% hydrochloric acid in water (590 μl) were added to the solution with stirring at room temperature. After 20 minutes, the reaction solution was neutralized with saturated aqueous sodium bicarbonate solution and subjected to solvent evaporation under reduced pressure. Saturated aqueous sodium bicarbonate solution was added to the residue, and the resulting solution was extracted with ethyl acetate and subjected to solvent evaporation under reduced pressure. The residue was purified by silica gel column chromatography (hexane/ethyl acetate=1:1→1:2) to yield compound 2-6 (420 mg, two-step yield: 73%) as a white foam.

Compound 2-6: $C_{24}H_{43}N_5O_5Si_2$ (MW=537.81)
white foam
ESI-HRMS (m/z):
calcd.: 560.2695 [M+Na]⁺
found: 560.2724
IR (cm⁻¹): 2953, 2928, 2856, 1739, 1646, 1591
¹³C-NMR (125 MHz, CDCl₃)
δ (ppm): 164.7, 155.6, 150.6, 149.7, 141.5, 121.1, 88.2, 84.4, 71.9, 62.9, 53.5, 42.0, 26.1, 25.9, 18.6, 18.2, −4.5, −4.7, −5.2, −5.4
¹H-NMR (400 MHz, CDCl₃)
δ (ppm):
8.28 (1H, s)
6.55 (1H, dd, J=6.4, 6.4 Hz)
5.73 (2H, s)
4.62 (1H, m)
4.00 (3H, s)
3.98 (1H, ddd, J=3.4, 3.4, 3.4 Hz)
3.88 (1H, dd, J=3.7, 11.3 Hz)
3.77 (1H, dd, J=3.1, 11.3 Hz)
2.58 (1H, ddd, J=6.5, 6.5, 6.5 Hz)
2.48 (1H, m)
0.90 (9H, s)
0.90 (9H, s)
0.09 (6H, s)
0.08 (6H, s)

(Step g) Synthesis of 6-(N-benzoylamino)-9-{(2R,4S,5R)-4-(tert-butyldimethylsilyloxy)-5-[(tert-butyldimethylsilyloxy)methyl]tetrahydrofuran-2-yl}-9H-purine-2-methylcarboxylate (compound 2-7)

Under an argon gas flow, anhydrous benzoic acid (105 mg, 0.4641 mmol) was added to a solution of compound 2-6 (50 mg, 0.0930 mmol) in anhydrous pyridine (470 μl), and the resulting mixture was stirred at 50° C. After 86 hours, the reaction solution was diluted with chloroform, and the resulting solution was washed with saturated aqueous ammonium chloride solution, dried on anhydrous sodium sulfate, and then subjected to solvent evaporation under reduced pressure. The residue was purified by silica gel column chromatography (hexane/ethyl acetate=3:1) to yield compound 2-7 (26.7 mg, 45%) as a white foam.

Compound 2-7: $C_{31}H_{47}N_5O_6Si_2$ (MW=641.92)
white foam
ESI-HRMS (m/z):
calcd.: 664.2957 [M+Na]⁺
found: 664.2939
IR (cm⁻¹): 2928, 2857, 1740, 1697, 1605, 1575, 1252
¹³C-NMR (125 MHz, CDCl₃)

δ (ppm): 164.9, 164.1, 152.5, 149.8, 149.6, 144.1, 133.3, 133.1, 129.0, 128.8, 128.2, 127.5, 125.3, 88.4, 84.7, 72.1, 63.0, 53.7, 42.0, 26.1, 25.9, 18.6, 18.2, −4.5, −4.7, −5.2, −5.3
$^1$H-NMR (400 MHz, CDCl$_3$)
δ (ppm):
9.01 (1H, s)
8.51 (1H, s)
8.01 (2H, d, J=7.6 Hz)
7.59 (1H, t, J=7.3 Hz)
7.50 (2H, t, J=7.5 Hz)
6.64 (1H, t, J=6.4 Hz)
4.63 (1H, m)
4.10 (1H, m)
4.04 (3H, s)
3.88 (1H, dd, J=3.8, 11.1 Hz)
3.78 (1H, dd, J=3.1, 11.3 Hz)
2.62 (1H, m)
2.51 (1H, m)
0.91 (9H, s)
0.89 (9H, s)
0.10 (6H, s)
0.07 (6H, s)

(Step h) Synthesis of 6-(N-benzoylamino)-9-{(2R, 4S,5R)-4-hydroxy-5-hydroxymethyl-tetrahydro-furan-2-yl}-9H-purine-2-methylcarboxylate (compound 2-8)

Under an argon gas flow, triethylamine (170 μl, 1.220 mmol) and triethylamine trihydrofluoride (200 μl, 1.227 mmol) were added at 0° C. to a solution of compound 2-7 (179 mg, 0.2789 mmol) in anhydrous pyridine (1 ml), and the resulting mixture was stirred at room temperature. After 9 hours, the reaction solution was purified by silica gel column chromatography (chloroform/methanol=50:1→45:1) to yield compound 2-8 (108.4 mg, 94%) as a white powder.
Compound 2-8: C$_{19}$H$_{19}$N$_5$O$_6$ (MW=413.39)
white powder
ESI-HRMS (m/z):
calcd.: 436.1228 [M+Na]$^+$
found: 436.1248
IR (cm$^{-1}$): 3350, 2932, 1730, 1608, 1521, 1261
$^{13}$C-NMR (125 MHz, DMSO)
δ (ppm): 165.7, 163.5, 152.2, 150.6, 149.1, 145.1, 133.0, 132.6, 128.6, 128.5, 127.1, 88.2, 83.7, 70.7, 61.5, 52.8
$^1$H-NMR (400 MHz, CD$_3$OD)
δ (ppm):
8.79 (1H, s)
8.08 (2H, d, J=7.0 Hz)
7.65 (1H, t, J=7.3 Hz)
7.55 (2H, dd, J=7.5, 7.5 Hz)
6.63 (1H, t, J=6.6 Hz)
4.64 (1H, m)
4.07 (1H, m)
4.01 (3H, s)
3.87 (1H, dd, J=3.4, 12.2 Hz)
3.79 (1H, dd, J=4.3, 12.2 Hz)
2.86 (1H, m)
2.53 (1H, m)

(Step i) Synthesis of 6-(N-benzoylamino)-9-{(2R, 4S,5R)-4-hydroxy-5-dimethoxytrityloxymethyl-tetrahydrofuran-2-yl}-9H-purine-2-methylcarboxylate (compound 2-9)

A solution of compound 2-8 (30 mg, 0.07257 mmol) in anhydrous pyridine (600 μl) was subjected to azeotropic distillation with anhydrous pyridine, and dimethoxytrityl chloride (49 mg, 0.1446 mmol) was added to the solution under an argon gas flow, and the resulting mixture was stirred at room temperature. After 75 minutes, the mixture was supplemented with methanol (1 ml) and stirred for further 10 minutes, and then subjected to solvent evaporation under reduced pressure. The residue was purified by silica gel column chromatography (chloroform/methanol=100:1) to yield compound 2-9 (49.5 mg, 95%) as a white powder.
Compound 2-9: C$_{40}$H$_{37}$N$_5$O$_8$ (MW=715.76)
white powder
ESI-MS (m/z):
calcd.: 716.27 [M+H]$^+$
found: 716.9859
$^1$H-NMR (500 MHz, CDCl$_3$)
δ (ppm):
8.96 (1H, s)
8.37 (1H, s)
8.04 (2H, dd, J=8.6, 8.6 Hz)
7.62 (1H, t, J=7.4 Hz)
7.53 (2H, dd, J=8.8, 16.3 Hz)
7.39 (2H, t, J=7.4 Hz)
7.3-7.2 (3H, m)
6.81 (4H, m)
6.67 (1H, m)
4.73 (1H, m)
4.15 (1H, m)
4.04 (3H, s)
3.78 (6H, s)
3.48 (1H, dd, J=4.5, 10.3 Hz)
3.41 (1H, dd, J=4.65, 10.4 Hz)
2.78 (1H, m)
2.68 (1H, m)
4.62 (1H, m)

(Step j) Synthesis of 6-(N-benzoylamino)-9-{(2R, 4S,5R)-4-[2-cyanoethoxy(diisopropylamino)phosphinyl]-5-dimethoxytrityloxymethyl-tetrahydrofuran-2-yl}-9H-purine-2-methylcarboxylate (compound 2-10)

A suspension of compound 2-9 (138 mg, 0.1928 mmol) in anhydrous dichloromethane (2.8 ml) was subjected to azeotropic distillation with toluene and anhydrous acetonitrile, and N,N-diisopropylethylamine (200 μl, 1.149 mmol) and 2-cyanoethyl-N,N-diisopropyl-chlorophosphoramidite (130 μl, 0.5828 mmol) were added to the suspension under an argon gas flow at 0° C., and the resulting mixture was stirred at 0° C. After 75 minutes, N,N-diisopropylethylamine (133 μl, 0.766 mmol) and 2-cyanoethyl-N,N-diisopropyl-chlorophosphoramidite (87 μl, 0.3885 mmol) were further added, and the resulting mixture was stirred for further 25 minutes, and the reaction solution was then diluted with chloroform. The solution was washed with saturated aqueous sodium bicarbonate solution and saturated brine, dried on anhydrous sodium sulfate, and then subjected to solvent evaporation under reduced pressure. The residue was purified by silica gel column chromatography (hexane/ethyl acetate=3:2→1:1→2:3). The residue was dissolved in dichloromethane, and recrystallization was performed by adding hexane cooled at −78° C. to the resulting solution, and the pellet was separated from supernatant and then dried under vacuum to yield compound 2-10 (120 mg, 68%) as a white foam.

Compound 2-10: $C_{49}H_{54}N_7O_9P$ (MW=915.98)
white foam
ESI-MS (m/z):
calcd.: 916.38 $[M+H]^+$
found: 915.9497
$^{31}$P-NMR (162 MHz, CDCl$_3$)
δ (ppm): 149.1
$^1$H-NMR (500 MHz, CDCl$_3$)
δ (ppm):
8.95 (1H, s)
8.02 (1H, s)
7.59 (2H, m)
7.53 (2H, m)
7.37 (2H, m)
7.30-7.15 (8H, m)
6.78 (4H, m)
6.66 (1H, m)
4.79 (1H, m)
4.28 (1H, m)
4.23-4.07 (2H, m)
4.04 (3H, s)
3.77 (6H, s)
3.55-3.42 (4H, m)
2.63 (1H, m)
2.44 (1H, m)

Introduction into 2'-Deoxyribooligonucleotide by Solid-Phase Synthesis

A solution of compound 2-10 in anhydrous acetonitrile was prepared and then loaded onto an automated DNA synthesizer to introduce compound 2-10 into a 2'-deoxyribooligonucleotide by a standardized protocol for the machine. To the nucleic acid probe synthesized and immobilized on CPG supports, anhydrous methanol and 4-aminopyridine were added, and the resulting mixture was incubated overnight at 55° C. for cleavage of the nucleic acid probe from the CPG supports, deprotection of the nucleotides, and introduction of amine. The methanol solvent was evaporated by blowing argon gas, and 0.1 M TEAA buffer was added to the residue, and the resulting solution was filtered through a membrane filter to remove insoluble material, and then purified by HPLC$^a$. Subsequently, the purified oligonucleotide in 5% acetic acid in water was left to stand at room temperature for 30 minutes for the deprotection of the dimethoxytrityl group at the 5' end, and the resulting oligonucleotide was again purified by HPLC$^b$ to obtain the derivative 4.

MALDI/TOF MS (negative ion mode)
calcd.: 4855.1296 $[M-H]^-$
found: 4856.045.
Conditions for HPLC$^a$:
Shiseido CAPCELL PAK C18, type MG, 4.6×250 mm; Solvent: A: 0.1M TEAA buffer, pH 7.0, Solvent B: CH$_3$CN, linear-gradient from 10% B to 40% B in 20 min; Column oven temperature: 35° C.; Flow rate: 1 ml/min; UV: 254 nm
Conditions for HPLC$^b$:
Shiseido CAPCELL PAK C18, type MG, 4.6×250 mm; Solvent: A: 0.1M TEAA buffer, pH 7.0, Solvent B: CH$_3$CN, linear-gradient from 10% B to 15% B in 20 min; Column oven temperature: 35° C.; Flow rate: 1 ml/min; UV: 254 nm The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

What is claimed is:

1. A labeling method for nucleic acid, comprising:

hybridizing a first nucleic acid probe that has a nucleotide sequence complementary to that of a nucleic acid to be labeled and contains a reactive nucleobase derivative incorporated at a position complementary to that of a target nucleobase as a target of labeling in the nucleic acid to be labeled, to the nucleic acid to be labeled;

transferring a transfer group contained in the reactive nucleobase derivative to the nucleotide residue containing the target nucleobase in the nucleic acid to be labeled; and labeling the transfer group transferred to the nucleotide residue with tritium, wherein in a case where the target nucleobase is a guanine nucleobase, the reactive nucleobase derivative is S-(2-(methylidene)-1-phenylbutane-1,3-dione)-6-thioguanine, in a case where the target nucleobase is a cytosine nucleobase, the reactive nucleobase derivative is S-(2-(methylidene)-1-phenylbutane-1,3-dione)-6-thioguanine or (E)-3-(1-(pyridin-2-yl)prop-2-en-1-one)-6-thioguanine, in a case where the target nucleobase is an adenine nucleobase, the reactive nucleobase derivative is (E)-3-(1-(pyridin-2-yl)prop-2-en-1-one)-4-thiothymine, and in a case where the target nucleobase is an uracil nucleobase, the reactive nucleobase derivative is N-(1-acetyl-4-pyridyl)-2-carboxamide-6-aminopurine.

2. The labeling method for nucleic acid according to claim 1, wherein in a case where the reactive nucleobase derivative is the (E)-3-(1-(pyridin-2-yl)prop-2-en-1-one)-6-thioguanine or the (E)-3-(1-(pyridin-2-yl)prop-2-en-1-one)-4-thiothymine, the transfer group is a pyridinyl-keto transfer group, and the pyridinyl-keto transfer group is transferred to the target nucleobase during the transferring.

3. The labeling method for nucleic acid according to claim 1, wherein in a case where the reactive nucleobase derivative is the S-(2-(methylidene)-1-phenylbutane-1,3-dione)-6-thioguanine, the transfer group is a diketo transfer group, and the diketo transfer group is transferred to the target nucleobase during the transferring.

4. The labeling method for nucleic acid according to claim 1, wherein in a case where the reactive nucleobase derivative is the N-(1-acetyl-4-pyridyl)-2-carboxamide-6-aminopurine, the transfer group is acetyl group, and an acetyl group is transferred to the 2' position of ribose of a nucleotide residue containing the target nucleobase during the transferring.

5. The labeling method for nucleic acid according to claim 1, further comprising:

hybridizing a second nucleic acid probe that has a nucleotide sequence complementary to that of the nucleic acid to be labeled and contains a reactive nucleobase derivative incorporated at a position complementary to that of a nucleobase different from the position of the target nucleobase in the nucleic acid to be labeled, to the nucleic acid to be labeled;

transferring a transfer group contained in the reactive nucleobase derivative of the second nucleic acid probe, which is hybridized to the nucleic acid to be labeled, to the nucleotide residue containing the nucleobase located at the different position in the nucleic acid to be labeled; and labeling the transfer group transferred to the nucleotide residue, which contains the nucleobase located at the different position, with a kind of radioactive material different from tritium.

* * * * *

SEQUENCE LISTING

<160> NUMBER OF SEQ ID NOS: 7

<210> SEQ ID NO 1
<211> LENGTH: 23
<212> TYPE: RNA
<213> ORGANISM: Artificial Sequence
<220> FEATURE:
<223> OTHER INFORMATION: RNA01

<400> SEQUENCE: 1
ccuauaaccu ugcauauaag ucc                23

<210> SEQ ID NO 2
<211> LENGTH: 17
<212> TYPE: DNA
<213> ORGANISM: Artificial Sequence
<220> FEATURE:
<223> OTHER INFORMATION: Probe for RNA01
<220> FEATURE:
<221> NAME/KEY: misc_feature
<222> LOCATION: (8)..(8)
<223> OTHER INFORMATION: n is a, c, g, or t

<400> SEQUENCE: 2
cttatatnca aggttat                17

<210> SEQ ID NO 3
<211> LENGTH: 25

```
<212> TYPE: RNA
<213> ORGANISM: Artificial Sequence
<220> FEATURE:
<223> OTHER INFORMATION: RNA02

<400> SEQUENCE: 3
ggacuuauau gcaagguuau aggga                                            25

<210> SEQ ID NO 4
<211> LENGTH: 15
<212> TYPE: DNA
<213> ORGANISM: Artificial Sequence
<220> FEATURE:
<223> OTHER INFORMATION: Probe for RNA02
<220> FEATURE:
<221> NAME/KEY: misc_feature
<222> LOCATION: (10)..(10)
<223> OTHER INFORMATION: n is a, c, g, or t

<400> SEQUENCE: 4
tataaccttn catat                                                       15

<210> SEQ ID NO 5
<211> LENGTH: 26
<212> TYPE: PRT
<213> ORGANISM: Artificial Sequence
<220> FEATURE:
<223> OTHER INFORMATION: Peptide

<400> SEQUENCE: 5

Met Ala Ser Met Thr Gly Gly Gln Gln Met Gly Thr Glu Phe Lys Thr
1               5                   10                  15

Ala Gln Asp Tyr Lys Asp Asp Asp Asp Lys
            20                  25

<210> SEQ ID NO 6
<211> LENGTH: 131
<212> TYPE: RNA
<213> ORGANISM: Artificial Sequence
<220> FEATURE:
<223> OTHER INFORMATION: mRNA

<400> SEQUENCE: 6
gggucuagag uuuaacuuua agaaggagau auacauaugg cuagcaugac ugguggacag      60
caaaugggua ccgaauucaa gaccgcgcaa gacuacaagg acgacgacga uaaguaguga     120
auaacuaauc c                                                          131

<210> SEQ ID NO 7
<211> LENGTH: 13
<212> TYPE: RNA
<213> ORGANISM: Artificial Sequence
<220> FEATURE:
<223> OTHER INFORMATION: Probe for mRNA
<220> FEATURE:
<221> NAME/KEY: misc_feature
<222> LOCATION: (7)..(7)
<223> OTHER INFORMATION: n is a, c, g, or u

<400> SEQUENCE: 7
ucuugcncgc ggu                                                         13
```